United States Patent
Claussen et al.

(10) Patent No.: US 9,791,150 B2
(45) Date of Patent: Oct. 17, 2017

(54) FLAME MONITORING OF A GAS TURBINE COMBUSTOR USING A CHARACTERISTIC SPECTRAL PATTERN FROM A DYNAMIC PRESSURE SENSOR IN THE COMBUSTOR

(71) Applicant: SIEMENS ENERGY, INC., Orlando, FL (US)

(72) Inventors: Heiko Claussen, North Brunswick, NJ (US); Nancy H. Ulerich, Longwood, FL (US); Zainul Momin, Winter Park, FL (US); Patrick Ronald Flohr, Mülheim a.d. Ruhr (DE)

(73) Assignees: SIEMENS ENERGY, INC., Orlando, FL (US); SIEMENS AKTIENGESELLSCHAFT, München (DE)

( * ) Notice: Subject to any disclaimer, the term of this patent is extended or adjusted under 35 U.S.C. 154(b) by 312 days.

(21) Appl. No.: 14/513,457

(22) Filed: Oct. 14, 2014

(65) Prior Publication Data

US 2015/0027211 A1 Jan. 29, 2015

Related U.S. Application Data

(63) Continuation-in-part of application No. PCT/EP2014/054524, filed on Mar. 10, 2014.

(30) Foreign Application Priority Data

Apr. 12, 2013 (EP) .................................... 13163529

(51) Int. Cl.
*G01M 15/00* (2006.01)
*F23M 11/04* (2006.01)
(Continued)

(52) U.S. Cl.
CPC ............. *F23M 11/045* (2013.01); *F23N 5/16* (2013.01); *F23N 5/242* (2013.01); *G01H 17/00* (2013.01);
(Continued)

(58) Field of Classification Search
USPC ....................................... 73/112.01
See application file for complete search history.

(56) References Cited

U.S. PATENT DOCUMENTS 3,263,423 A * 8/1966 Gorzegno ............... F01K 23/06 122/1 B
5,544,478 A 8/1996 Shu et al.
(Continued)

FOREIGN PATENT DOCUMENTS

EP 1116945 A2 7/2001
EP 1116946 A2 7/2001
(Continued)

OTHER PUBLICATIONS

Non-patent literature citations 1-9 are of related applications before the US Patent and Trademark Office: "Active Temperature Monitoring In Gas Turbine Combustors", filed on Dec. 18, 2013, U.S. Appl. No. 14/132,001.
(Continued)

*Primary Examiner* — Eric S McCall
*Assistant Examiner* — Mohammed E Keramet-Amircola

(57) ABSTRACT

The state of a flame in a gas turbine engine combustor is acoustically monitored using a dynamic pressure sensor within the combustor. A spectral pattern of a dynamic pressure sensor output signal from the sensor is compared with a characteristic frequency pattern that includes information about an acoustic pattern of the flame and information about acoustic signal canceling due to reflections within the combustor. The spectral pattern may also be compared
(Continued)

with a characteristic frequency pattern including information about a flame-out condition in the combustor.

20 Claims, 17 Drawing Sheets

(51) Int. Cl.
| | |
|---|---|
| *F23N 5/16* | (2006.01) |
| *F23N 5/24* | (2006.01) |
| *G01L 19/06* | (2006.01) |
| *G01M 15/14* | (2006.01) |
| *G01N 29/36* | (2006.01) |
| *G01N 29/44* | (2006.01) |
| *G01H 17/00* | (2006.01) |
| *G01K 11/22* | (2006.01) |
| *G01N 29/00* | (2006.01) |

(52) U.S. Cl.
CPC .......... *G01K 11/22* (2013.01); *G01L 19/0663* (2013.01); *G01M 15/14* (2013.01); *G01N 29/00* (2013.01); *G01N 29/36* (2013.01); *G01N 29/44* (2013.01); *F23N 2025/04* (2013.01); *F23N 2029/16* (2013.01); *F23N 2031/06* (2013.01); *F23N 2041/20* (2013.01); *G01N 2291/0217* (2013.01); *G01N 2291/0254* (2013.01); *Y02T 50/677* (2013.01)

(56) References Cited

U.S. PATENT DOCUMENTS

| | | | |
|---|---|---|---|
| 5,719,791 | A | 2/1998 | Neumeier et al. |
| 5,784,300 | A | 7/1998 | Neumeier et al. |
| 6,273,064 | B1 | 8/2001 | Scholl et al. |
| 6,840,218 | B2 | 1/2005 | Scholl et al. |
| 6,976,351 | B2 | 12/2005 | Catharine et al. |
| 7,148,611 | B1 | 12/2006 | Liu |
| 7,210,297 | B2 | 5/2007 | Shah et al |
| 7,503,177 | B2 | 3/2009 | Bland et al. |
| 7,743,599 | B2 | 6/2010 | Taware et al. |
| 7,853,433 | B2 | 12/2010 | He et al. |
| 7,927,095 | B1 | 4/2011 | Chorpening et al. |
| 9,453,784 | B2* | 9/2016 | DeSilva ................ G01K 11/24 |
| 9,709,448 | B2* | 7/2017 | DeSilva ................ G01K 11/24 |
| 2003/0145829 | A1 | 8/2003 | Scholl et al. |
| 2005/0107942 | A1 | 5/2005 | Nomura et al. |
| 2006/0074496 | A1* | 4/2006 | Taware ................... G05B 9/02 700/11 |
| 2006/0137353 | A1 | 6/2006 | Lieuwen et al. |
| 2006/0218933 | A1* | 10/2006 | Schuermans .......... F23N 1/002 60/776 |
| 2007/0119147 | A1 | 5/2007 | Cornwell et al. |
| 2007/0199328 | A1 | 8/2007 | Shah et al. |
| 2008/0010966 | A1 | 1/2008 | Taware et al. |
| 2009/0299695 | A1 | 12/2009 | Subbu et al. |
| 2010/0076698 | A1* | 3/2010 | He ........................ F23N 5/242 702/35 |
| 2012/0150413 | A1 | 6/2012 | Bunce et al. |
| 2012/0279229 | A1* | 11/2012 | Zinn ....................... F02C 7/057 60/773 |
| 2014/0053574 | A1 | 2/2014 | McConkey |

FOREIGN PATENT DOCUMENTS

| | | |
|---|---|---|
| EP | 1293764 A2 | 3/2003 |
| EP | 1321655 A1 | 6/2003 |
| EP | 1605205 A2 | 12/2005 |
| EP | 1632718 A2 | 3/2006 |
| EP | 1752637 A2 | 2/2007 |
| EP | 1870680 A2 | 12/2007 |
| EP | 1209458 B1 | 1/2008 |
| EP | 2211102 A2 | 7/2010 |
| EP | 2249005 A2 | 11/2010 |
| FR | 2872282 A1 | 6/2004 |
| WO | W09514226 A1 | 5/1995 |
| WO | W02010036285 A1 | 4/2010 |

OTHER PUBLICATIONS

"Temperature Measurement in a Gas Turbine Engine Combustor", filed on Mar. 14, 2013, U.S. Appl. No. 13/804,132.
"Active Measurement of Gas Flow Temperature, Including in Gas Turbine Combustors", filed on Mar. 13, 2014, U.S. Appl. No. 14/207,741.
"Multi Functional Sensor System for Gas Turbine Combustion Monitoring and Control" filed on Dec. 18, 2013, U.S. Appl. No. 14/109,992.
"Nonintrusive Performance Measurement of a Gas Turbine Engine in Real Time", filed on Jul. 28, 2014, U.S. Appl. No. 14/341,950.
"Nonintrusive Transceiver and Method for Characterizing Temperature and Velocity Fields in a Gas Turbine Combustor", filed on Jul. 28, 2014, U.S. Appl. No. 14/341,924.
"Active Measurement of Gas Flow Velocity or Simultaneous Measurement of Velocity and Temperature, Including in Gas Turbine Combustors" filed on Mar. 13, 2014, U.S. Appl. No. 14/207,803.
"Single Dynamic Pressure Sensor Based Flame Monitoring of a Gas Turbine Combustor", filed concurrently herewith.
"Flame Monitoring of a Gas Turbine Combustor Using Multiple Dynamic Pressure Sensors in Multiple Combustors", filed concurrently herewith.
"Signature Extraction Using Mutual Interdependencies", Heiko Claussen, et al., Pattern Recognition, vol. 44, Issue 3, ISSN 0031-3203, pp. 650-661, Mar. 2011.
"Combustion Dynamics Instrumentation", IMI Sensors, A PCB Piezotronics Div., 2010 PCB Group, Inc.

* cited by examiner

FLAME MONITORING OF A GAS TURBINE COMBUSTOR USING A CHARACTERISTIC SPECTRAL PATTERN FROM A DYNAMIC PRESSURE SENSOR IN THE COMBUSTOR

CROSS-REFERENCE TO RELATED APPLICATIONS

This application is a continuation in part of copending International Application PCT/EP2014/054524 entitled "Method for Monitoring a Flame State," filed on Mar. 10, 2014, which claims priority to European Patent Application Serial No. 13163529.4 filed on Apr. 12, 2013.

This application incorporates by reference the following co-pending United States utility patent applications in their entirety as if fully set forth herein:

"Single Dynamic Pressure Sensor Based Flame Monitoring of a Gas Turbine Combustor", filed concurrently herewith, Ser. No. 14/513,316;

"Flame Monitoring of a Gas Turbine Combustor Using Multiple Dynamic Pressure Sensors in Multiple Combustors", filed concurrently herewith, Ser. No. 14/513,373;

"Nonintrusive Performance Measurement of a Gas Turbine Engine in Real Time", filed on Jul. 28, 2014, Ser. No. 14/341,950;

"Nonintrusive Transceiver and Method for Characterizing Temperature and Velocity Fields in a Gas Turbine Combustor", filed on Jul. 28, 2014, Ser. No. 14/341,924;

"Active Measurement Of Gas Flow Temperature, Including In Gas Turbine Combustors", filed on Mar. 13, 2014, Ser. No. 14/207,741;

"Active Measurement of Gas Flow Velocity or Simultaneous Measurement of Velocity and Temperature, Including in Gas Turbine Combustors" filed on Mar. 13, 2014, Ser. No. 14/207,803;

"Active Temperature Monitoring In Gas Turbine Combustors", filed on Dec. 18, 2013, Ser. No. 14/132,001;

"Multi-Functional Sensor System For Gas Turbine Combustion Monitoring And Control" filed on Dec. 18, 2013, Ser. No. 14/109,992;

"Temperature Measurement In A Gas Turbine Engine Combustor", filed on Mar. 14, 2013, Ser. No. 13/804,132; and "Gas Turbine Engine Control Using Acoustic Pyrometry", filed on Dec. 14, 2010, Ser. No. 12/967,148, Publication No. US2012/0150413.

This application also incorporates by reference in its entirety as if fully set forth herein U.S. Pat. No. 7,853,433, "Combustion Anomaly Detection Via Wavelet Analysis Of Dynamic Sensor Signals", issued Dec. 14, 2010.

BACKGROUND OF THE INVENTION

1. Field of the Invention

The invention relates to a method and apparatus for monitoring a flame state in a combustion chamber of a gas turbine using dynamic pressure sensors. More specifically, it relates to the use of a dynamic pressure sensor arranged in a pressure influence zone in a combustor of the combustion chamber, and comparing a spectral pattern of the sensor output signal to a characteristic frequency pattern that includes information about an acoustic pattern of the flame and information about acoustic signal canceling due to reflections within the combustor.

2. Description of the Prior Art

A gas turbine is a flow machine in which a pressurized gas expands. It comprises a turbine or expander, a compressor connected upstream thereof, and a combustion chamber positioned therebetween. The operating principle is based on the cycle process (Joule process): This compresses air by way of the blading of one or more compressor stages, subsequently mixes said air in the combustion chamber with a gaseous or liquid fuel, ignites and combusts the same. The air is also conducted into a secondary air system and utilized for cooling in particular components that are subject to extreme thermal stresses.

This results in a hot gas (mixture composed of combustion gas and air) which expands in the following turbine section, with thermal energy being converted into mechanical energy in the process and in the first instance driving the compressor. The remaining portion is employed in the shaft driving mechanism for driving a generator, a propeller or other rotating loads. In the case of the jet power plant, on the other hand, the thermal energy accelerates the hot gas stream, which generates the thrust.

Typically, a plurality of combustors is provided, arranged annularly around the turbine axis and having corresponding injector nozzles for fuel. In such a configuration the combustors can be arranged as individual combustors, referred to as baskets, which are connected only shortly before the entry into the turbine (referred to as a can or can-annular design), or the combustors can be arranged in a common ring-shaped combustion chamber (referred to as an annular design). When the gas turbine is started up, the fuel-air mixture in the respective combustion chamber is ignited by means of igniters. Thereafter the combustion takes place continuously.

The continuous monitoring of the flame, in particular in each individual combustor in the case of the can-type or can-annular-type design, is important for the operational safety of the gas turbine in order to avoid dangerous situations due to the ingress of unburnt fuel in the combustion chamber or the turbine outlet. In this case the monitoring of the flame state must be performed quickly so that no dangerous air-fuel mixtures are produced over a relatively long period of time. Response times of less than a second are desirable. In particular the igniting and extinguishing of flames must be reliably detected at any given time, especially also in situations such as a load throw-off, during powering down of the gas turbine, or in partial extinguishing of individual flames.

Optical and temperature-based systems are known for monitoring the flame state. Optical systems measure the light emitted by the flame directly and typically are comparatively quick. A disadvantageous aspect with systems of said type, however, is the susceptibility of the optical components to soiling by particles, dust, soot, oil, as well as water and condensation. The soiling reduces the flame detection capabilities of such systems as well as their reliability and operational availability.

As an alternative to such optical systems, systems have therefore been developed which are based on the dynamic measurement of the pressure in the pressure influence zone. A system of said type is described for example in U.S. Pat. No. 7,853,433 B2. In this case a piezoelectric pressure sensor is arranged in the pressure influence zone of each combustor. The time signal of the pressure sensor is digitized and subjected to a wavelet analysis. The wavelet analysis enables the flame state and a flame flashback to be detected based on the comparison of the normalized amplitudes of the wavelet coefficients with predetermined threshold amplitudes. In this case the signals are normalized using the mean value of all of the combustors, as a result of which the threshold value is specified. If said threshold values are exceeded it signifies a deviation from the normal state and consequently a change in the flame state, either the igniting or extinguishing of the flame or a flame flashback.

However, the method described in U.S. Pat. No. 7,853, 433 B2 has the disadvantage that certain flame states are not detected. An extinction of all of the combustor flames will not be detected, for example.

To reduce costs it is desired to use already existing sensors for flame monitoring. Dynamic pressure sensors are available from the monitoring of the combustion dynamics and can be used for flame monitoring. Some current combustion dynamics monitoring systems utilize two dynamic pressure sensors per combustor. Future gas turbines will potentially utilize only one dynamic pressure sensor per combustor. To prevent the need for additional instrumentation and thus to keep a cost advantage, a need exists in the art to detect and monitor a turbine combustor flame using a single sensor per combustor.

A further need exists in the art to detect a condition of simultaneous flame-out in all combustors using a single sensor per combustor.

There is an additional need in the art to filter the acoustic data received from a sensor in a combustor to focus the analysis on specific, localized sound sources while disregarding background noise.

SUMMARY OF THE INVENTION

Accordingly, it is therefore the object of the invention to provide a more reliable and more accurate detection of the flame state for each individual flame in the combustion chamber of a gas turbine.

It is a further object of the invention is to provide methods and systems for detecting and monitoring flames in individual combustors of a gas turbine combustor chamber wherein only a single sensor is present in each combustor.

Another object of the invention is to detect and monitor a combustor flame based on the spectral content of acoustic oscillations emitted by the flame.

Exemplary embodiments of the invention feature a method for monitoring a flame in a gas turbine engine combustor. A dynamic pressure sensor output signal is received from an acoustic sensor positioned in the gas turbine engine combustor. The output signal is indicative of acoustic oscillations within the combustor. A first comparison is made of a spectral pattern of the dynamic pressure sensor output signal with a characteristic frequency pattern that includes information about an acoustic spectral pattern of the flame and information about acoustic signal canceling due to reflections of the dynamic pressure sensor output signal within the combustor. Based on the first comparison, a determination is made whether a flame is present in the combustor.

The characteristic frequency pattern may be constructed by recording a first training spectral pattern of the dynamic pressure sensor output signal while the flame is burning; recording a second training spectral pattern of the dynamic pressure sensor output signal while the flame is not burning; and performing a feature extraction analysis operation on the first and second training spectral patterns to identify a spectral characteristic that links a spectral pattern to a flame state. In that case, making the determination whether a flame is present in the combustor further comprises evaluating a similarity of the spectral characteristic to the spectral pattern of the dynamic pressure sensor output signal.

Other exemplary embodiments of the invention feature a system for monitoring a flame in a gas turbine engine combustor. The system includes an acoustic sensor positioned for measuring acoustic oscillations within the gas turbine engine combustor, and a processor connected for receiving a dynamic pressure sensor output signal from the acoustic sensor. The system further includes computer readable media containing computer readable instructions that, when executed by the processor, cause the processor to perform the following operations: receiving a dynamic pressure sensor output signal from the acoustic sensor, the output signal being indicative of acoustic oscillations within the combustor; making a first comparison of a spectral pattern of the dynamic pressure sensor output signal with a characteristic frequency pattern that includes information about an acoustic spectral pattern of the flame and information about acoustic signal canceling due to reflections of the dynamic pressure sensor output signal within the combustor; and, based on the first comparison, making a determination whether a flame is present in the combustor.

The respective objects and features of the exemplary embodiments of the invention may be applied jointly or severally in any combination or sub-combination by those skilled in the art.

BRIEF DESCRIPTION OF THE DRAWINGS

The invention is explained in more detail with reference to an exemplary embodiment illustrated in a drawing, in which.

Like parts are labeled with the same reference signs in all the figures.

DETAILED DESCRIPTION

Figure 1:
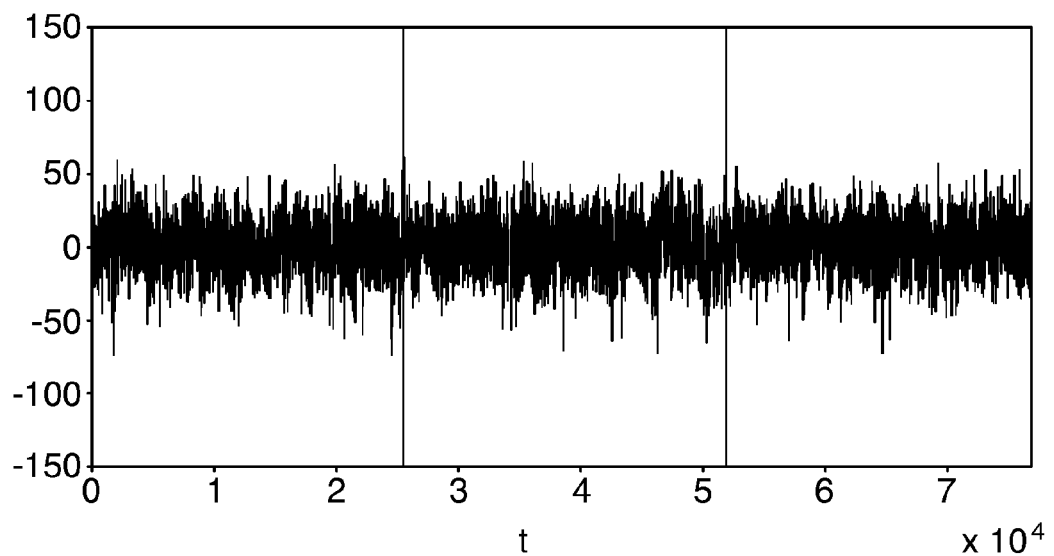
FIG. 1 shows time signals of two dynamic pressure sensors in the flame exit region of a combustor.

FIG. 1 shows the signals of two dynamic pressure sensors which are based on piezoelectricity in order to provide an optimal, precise pressure measurement. Alternatively, sensors of a different type may be used as pressure sensors provided they permit the current pressure value to be inferred, for example thermocouple elements whose signal also has a dependent relationship with the pressure signal. The dynamic pressure sensors are arranged at two different locations in the pressure influence zone of a combustor in a gas turbine. What is understood by pressure influence zone in this context is an area whose pressure fluctuations are dependent to a large extent on the dynamics of the flame of the respective combustor. In the case of a gas turbine of the can-annular type this can be for example an area within the respective basket of the combustor. The pressure sensors are typically arranged upstream of the flame. The gas turbine is explained in detail below with reference to FIG. 8.

FIGS. 1 to 6 each show graphs. In FIG. 1, the signal of each of the two dynamic pressure sensors is plotted against time. Because the signals of the pressure sensors are digitized in the method execution sequence described in detail in FIG. 7, the scale of the abscissa in this case is held directly in 10,000 sampling points. The sampling frequency is 25600 Hz in this case. FIG. 1 shows three succeeding data blocks, each 1 second long. Shorter data blocks of 0.6 or 0.3 seconds in length are used in the method, which means that in the latter case an evaluation can take place every 0.3 seconds.

However, the evaluation is not necessarily performed serially, but rather the time periods may also overlap. Thus, for example, data blocks having a length of 0.6 seconds can be evaluated every 0.3 seconds. This enables a fast response speed of the evaluation while at the same time delivering good statistics.

Figure 2:
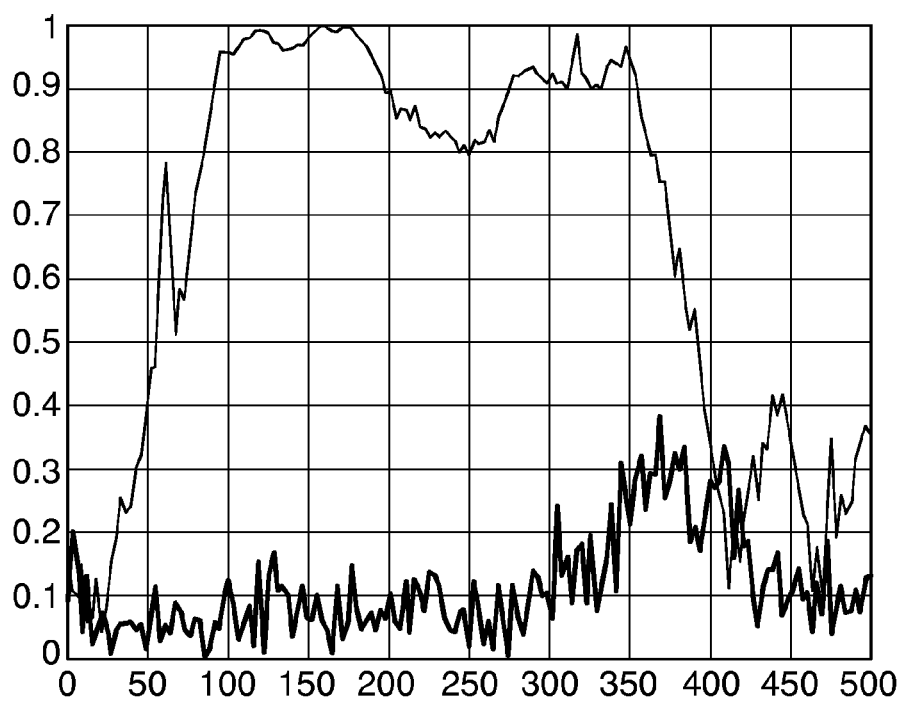
FIG. 2 shows the coherence function of the two time signals in two time segments.

FIG. 2 shows an example of a filtering of the signals of one data block from FIG. 1 in each case. Two time signals in one data block, i.e. in a common time segment, are Fourier-transformed and their coherence function calculated. The formula of the coherence function reads:

$$\gamma = \sqrt{\frac{G_{xy}^2}{G_{xx}G_{yy}}}.$$

Two coherence functions of different data blocks whose values can lie between 0 and 1 are plotted in the graph of FIG. 2, specifically once for a burning flame (upper curve) and once for an extinguished flame (lower curve). The coherence functions are plotted in the range from 0 to 500 Hz in each case.

FIG. 2 clearly illustrates the significantly higher coherence of the signals in the case of a burning flame. The coherence function lies above 0.8 in a wide range from approx. 80 to 350 Hz, whereas in the case of an extinguished flame it never climbs above 0.4.

Figure 7:
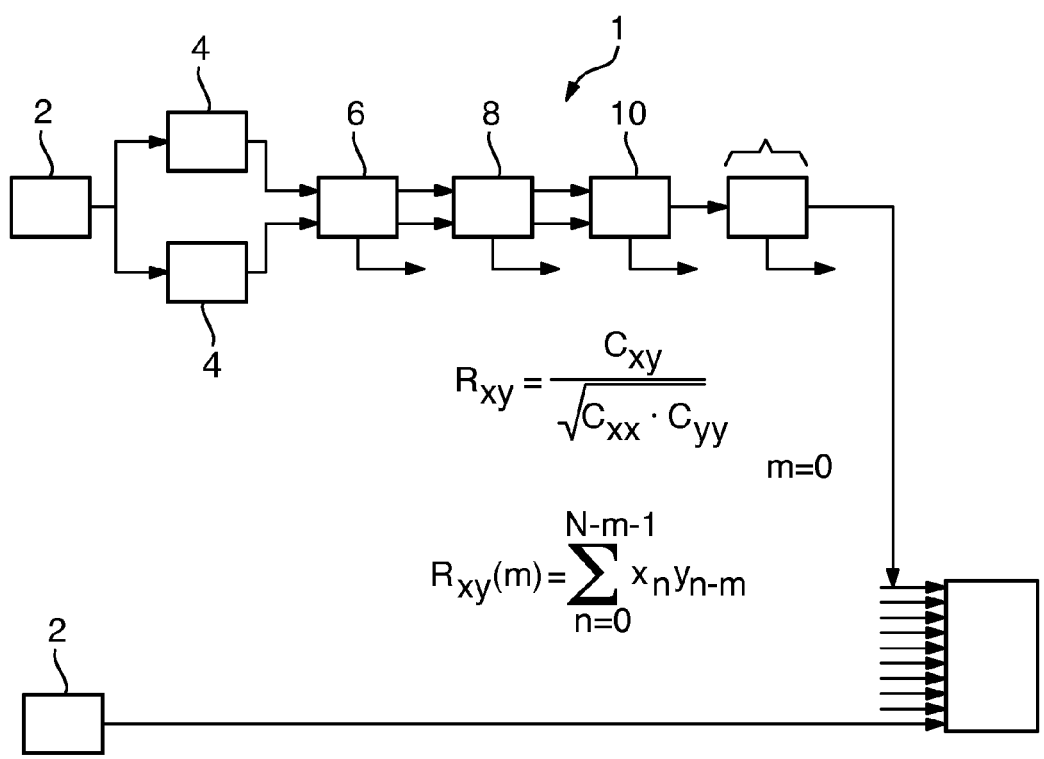
FIG. 7 is a block diagram of a method for monitoring a flame state in a gas turbine.

The coherence function shown in FIG. 2 is used in the sequence described in FIG. 7 for filtering the signal. Outside of ranges in which the coherence in the case of a burning flame is higher than 0.8, the amplitudes of the frequencies in the Fourier-transformed data blocks are set to 0. Subsequently the thus processed respective data blocks are transformed back into the time domain once more by means of an inverse Fourier transform and processed further there.

The signals now present in the time domain once again are now processed further for each data block and each combustor. The correlation coefficient is formed continuously from the two signals of each combustor, per data block in each case, so that an up-to-date correlation coefficient is present every 0.3 seconds. Variations with time of the correlation coefficients are shown in FIGS. 3 to 6.

Figure 3:
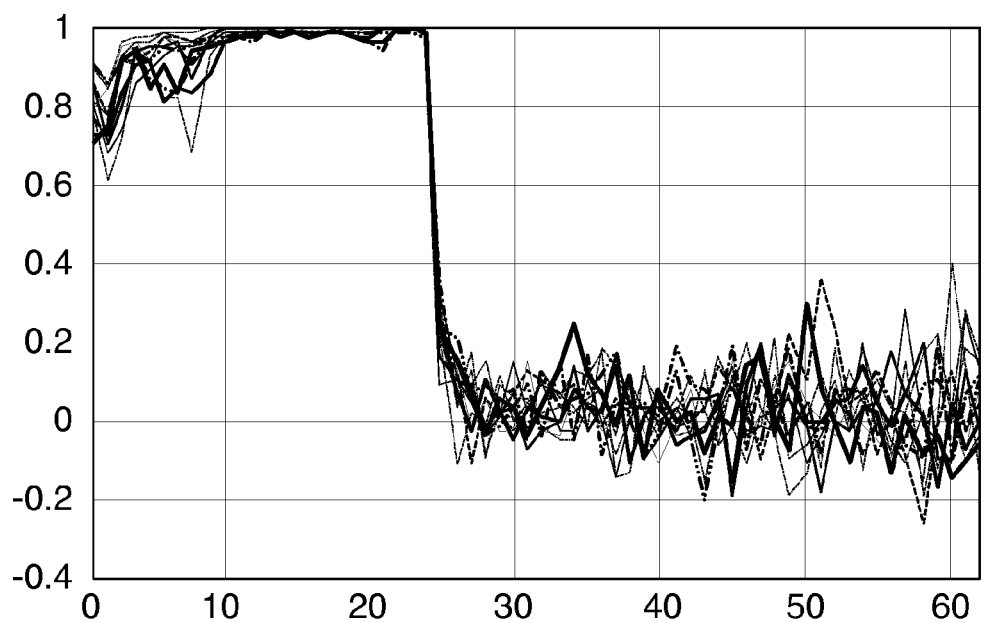
FIG. 3 shows the evolution in time of the correlation coefficient of the two filtered time signals in the case of a load throw-off.
Figure 4:
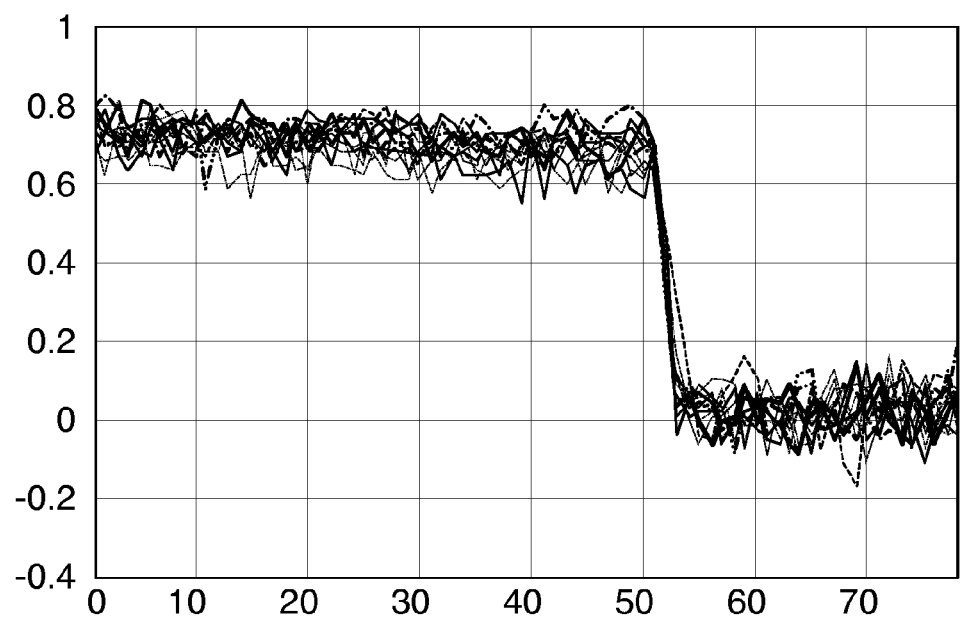
FIG. 4 shows the evolution in time of the correlation coefficient of the two filtered time signals in the case of a controlled gas turbine shutdown.
Figure 5:
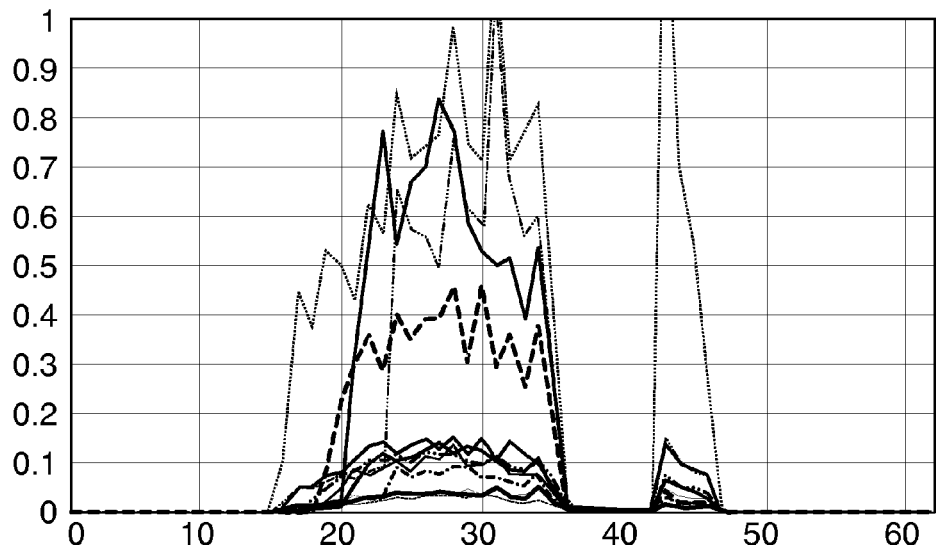
FIG. 5 shows the evolution in time of the correlation coefficient of a plurality of combustors during the ignition sequence.

FIGS. 3 to 5 show the variation with time of the correlation coefficients for a total of twelve different combustors. The correlation coefficient is plotted against the time in seconds in each case. A fixed band pass filtering of the signals was carried out between 40 and 600 Hz in each case.

FIG. 3 shows the variation with time for a so-called trip, i.e. a fast shutdown as a consequence, for example, of a threshold value for an operating parameter such as the rotational speed being exceeded. At approx. 24 seconds, a fast shutdown of the gas turbine is executed with interruption of the fuel supply to the combustors. The graph shows an increase in the coherence up to practically the value 1 from second 10, which signifies a high flame intensity. This corresponds to the expected highly dynamic state during a trip. From the moment of the fast shutdown in which the flames are extinguished, the coherence decreases rapidly and oscillates around zero. Most of the deflections in this case are below 0.2, with the correlation coefficient never deflecting above 0.4.

FIG. 4 shows the variation with time of the correlation coefficients of the combustors for a routine controlled shutdown of the gas turbine. During routine operation the correlation coefficients vary between 0.6 and 0.8. In the event of a shutdown of the gas turbine with stopping of the fuel supply to the combustors at second 52, the correlation coefficient drops rapidly to values below 0.2. The flames are extinguished.

FIG. 5 shows the variation with time of the correlation coefficients for the ignition phase, i.e. the startup of the gas turbine. The first ignition takes place at second 15. The exaggerated increase in the correlation coefficients of a total of four combustors compared to the other combustors is clearly recognizable. Only these combustors have ignited in the first step, because their correlation coefficients increase significantly above a value of 0.2. The ignition time points are likewise clearly to be differentiated, as also is the extinction of the flames at second 35. At the time of the second ignition around second 43 it is apparent that only a single combustor ignites.

Figure 6:
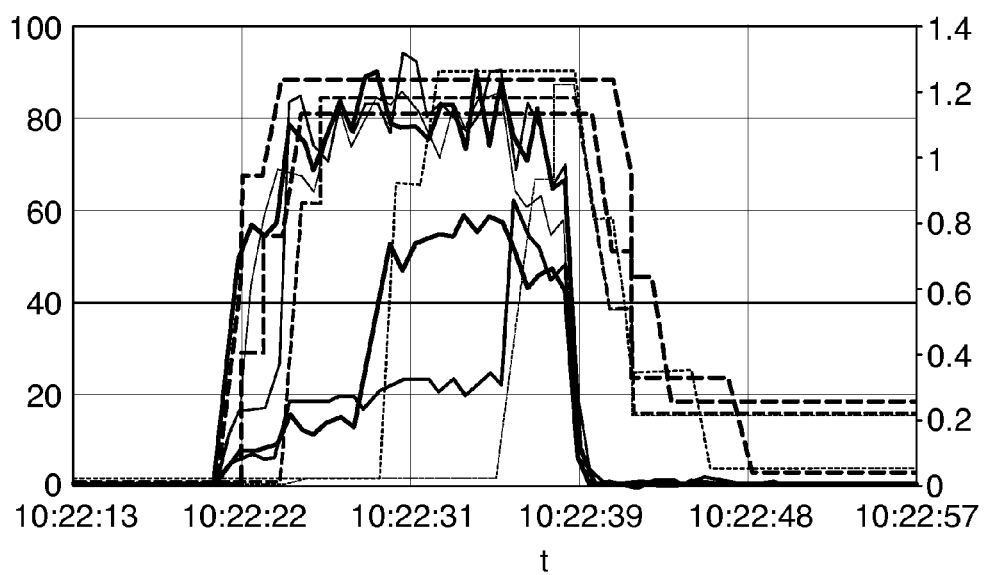
FIG. 6 shows the evolution in time of the correlation coefficient of a plurality of combustors during the ignition sequence in comparison with data of optical sensors.

FIG. 6 shows an alternative method of monitoring during the ignition sequence. In this instance the root mean squares of the oscillations have been determined during the data block and weighted with the correlation coefficient. This value is marked on the right-hand ordinate and corresponds in a range from 0 to 1.4 to a flame intensity of 0% to 100% plotted on the left-hand ordinate. In this case the threshold value for the igniting of the flame has been set to a flame intensity of 40%. One skilled in the art will recognize that other weighted representations of the oscillations may be used, such as a logarithm representation or a sinusoidal weighted representation.

The figure shows the root mean squares, weighted with the correlation coefficient, of the pressure sensors of different combustors (unbroken lines) in comparison with values from optical sensors (dashed lines, same line thicknesses correspond to same combustors in each case). The time axis is specified here in hours:minutes:seconds. During the ignition sequence the curves determined as described from the pressure sensors infringe the threshold value up to 1 second earlier than the values determined from the optical sensors. The igniting of the flame is therefore detected more quickly. This difference becomes even clearer at the time of the flame extinction approximately from 10:22:37. In this case the values obtained from the pressure sensors are below the threshold value by up to 5 seconds before the values obtained from the optical sensors. The detection of an extinguishing flame is considerably faster with the described method and consequently increases the operational safety of the gas turbine significantly.

It holds in all of the above-cited applications of the method that the selected threshold values can be adaptively adjusted for different modes of operation of the gas turbine. In one embodiment variant, for example, other threshold values can apply for the powering up of the gas turbine when the combustor flames are ignited than during ongoing operation. This enables empirical values to be taken into account with regard to the different flame dynamics.

FIG. 7 summarizes the method 1 in a block diagram: For each combustor 2 of the gas turbine two piezoelectric-based dynamic pressure sensors 4 exist at two different positions in the pressure influence zone thereof. Since the arrangement and the method are identical for all of the combustors 2, the method is fully illustrated using only the example of the combustor 2 depicted in the upper part of the drawing. The remaining eleven combustors 2 in the exemplary embodiment are consolidated as a single combustor 2 in the block diagram.

The signals of the two pressure sensors 4 are input into an A/D converter 6 and digitized. A sampling frequency of 25600 Hz is used in this case. Subsequently the digitized data is input into a preprocessing module 8. Here, the data is divided into data blocks of the respective time segment that are approx. 0.3 to 0.6 seconds long. For each data block, filtering takes place using a fixed bandpass filter between for example 80 and 350 or 80 and 600 Hz and/or using the dynamic method by way of the coherence of simultaneous data blocks as described in FIG. 2. Suitable resolutions for the Fourier transforms that are necessary here lie between 1 and 6 Hz.

The filtered data blocks having a length of 0.3 to 0.6 seconds are input into a calculation module 10. There, the correlation coefficient is formed from the simultaneous data blocks during ongoing operation (upper formula), while root mean squares weighted with the correlation coefficient are formed during the startup phase (lower formula). A value thus results per combustor for each data block and hence time segment. Said value is input into an evaluation module 12.

As soon as the input value climbs above 0.4, "Flame ON", i.e. flame active, is output as the output signal. If the value drops below 0.2, the output signal is output as "Flame OFF", i.e. flame extinguished. In this case averaging over at least two consecutive data blocks can also be performed in addition in the evaluation module 12 in order to minimize statistical fluctuations. The averaging can also take place continuously over a plurality of data blocks and be provided with an e.g. exponential weighting so that current data blocks are weighted higher. The use of threshold output signal values is merely exemplary. Other measures, such as the steepness of a drop over time or the difference between results from different combustors, may alternatively be used.

Figure 8:
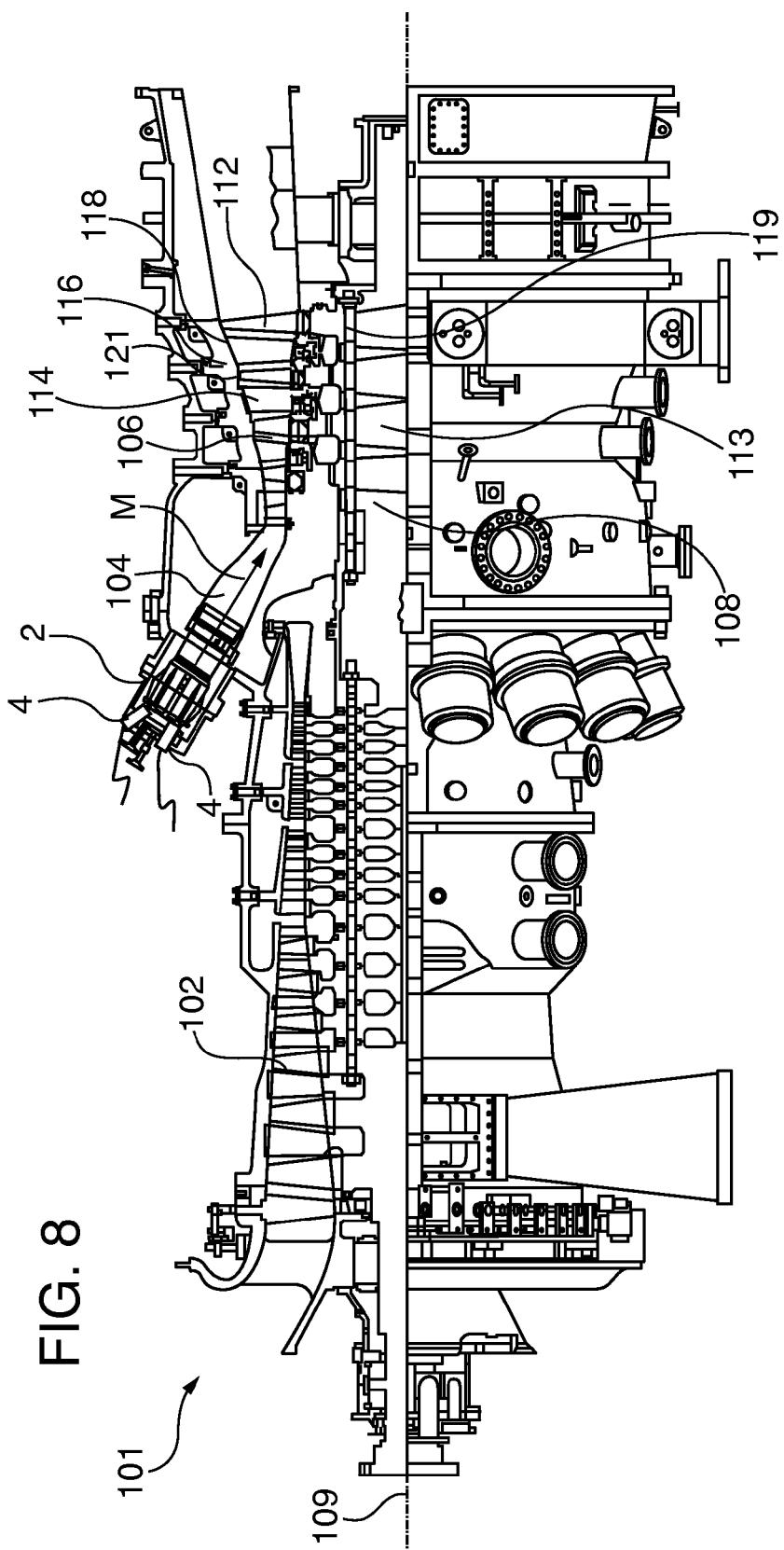
FIG. 8 shows a gas turbine.

FIG. 8 shows the gas turbine 101. The lower half of FIG. 8 shows a view from above, the upper half a cross-sectional view. A gas turbine 101 is a flow machine. It has a compressor 102 for combustion air, a combustion chamber 104, as well as a turbine unit 106 for driving the compressor 102 and a generator (not shown) or a work machine. Toward that end the rotating parts of turbine unit 106 and compressor 102 are arranged on the rotor 108, to which the generator or work machine is also connected and which is rotatably mounted around its central axis 109. The combustion chamber 104 implemented in a can-annular design in the exemplary embodiment comprises a number of tube-shaped individual combustors 2 which may include baskets. Each of the combustors 2 is equipped for combusting a liquid or gaseous fuel.

The turbine unit 106 has a number of rotatable moving blades 112. The moving blades 112 are part of the rotor 108 and are arranged annularly on turbine disks 113, thus forming a number of moving blade rings or rows. In addition the turbine unit 106 comprises a number of stationary guide vanes 114 which are likewise mounted annularly to a guide vane carrier 116 of the turbine unit 106, thus forming guide vane rows. In this arrangement the moving blades 112 serve to drive the rotor 108 through transfer of momentum from the working medium M flowing through the turbine unit 106. The guide vanes 114, in contrast, serve to guide the flow of the working medium M between in each case two succeeding moving blade rows or moving blade rings, viewed in the flow direction of the working medium M. A succeeding pair consisting of a ring of guide vanes 114 or a guide vane row and of a ring of moving blades 112 or a moving blade row is also referred to in this context as a turbine stage.

Each guide vane 114 has a platform 118 which is arranged as a wall element for fixing the respective guide vane 114 to a guide vane carrier 116 of the turbine unit 106.

Each moving blade 112 is mounted in an analogous manner on a turbine disk 113 by way of a platform 119, which is also referred to as a blade root. In such an arrangement the platforms 118, 119 are components that are subject to comparatively severe thermal stresses and form the outer boundary of a hot gas duct for the working medium M flowing through the turbine unit 106. The rotor 1, which is enclosed by the hot gas duct, is also subject to extreme thermal stresses, in particular during transient processes such as the startup of the gas turbine 101.

A ring segment 121 is arranged in each case on a guide vane carrier 116 of the turbine unit 106 between the platforms 118, arranged spaced at a distance from one another, of the guide vanes 114 of two adjacent guide vane rows. The outer surface of each ring segment 121 is in this case likewise exposed to the hot working medium M flowing through the turbine unit 106 and in the radial direction is spaced apart by a gap from the outer end of the moving blades 112 disposed opposite thereto. The ring segments 121 arranged between adjacent guide vane rows in this case serve in particular as cover elements which protect the inner housing in the guide vane carrier 116 or other built-in housing parts from excessive thermal stress due to the hot working medium M flowing through the turbine 106.

As already described, the combustion chamber 104 is embodied in the exemplary embodiment as what is termed a can-annular combustion chamber, in which a plurality of combustors 2 arranged around the rotor 1 in the circumferential direction are arranged individually, leading into the turbine unit 106 on the outlet sides. Here, two described pressure sensors 4 per combustor 2 are arranged in each case in the respective pressure influence zone thereof, in this instance upstream of the fuel inlet. The shape of the combustion chamber is not critical for the applicability of the above-described method. The method is equally suitable for use in gas turbines 101 having other combustion chamber shapes such as e.g. annular-type combustion chambers.

If only one pressure sensor 4 is provided per combustor 2 or if one pressure sensor 4 fails, the signal of an adjacent combustor 2 can alternatively be used for the correlation calculation or an autocorrelation of the signals of the same pressure sensor 4 can be calculated and used. This is shown in FIGS. 9 and 10.

Figure 9:
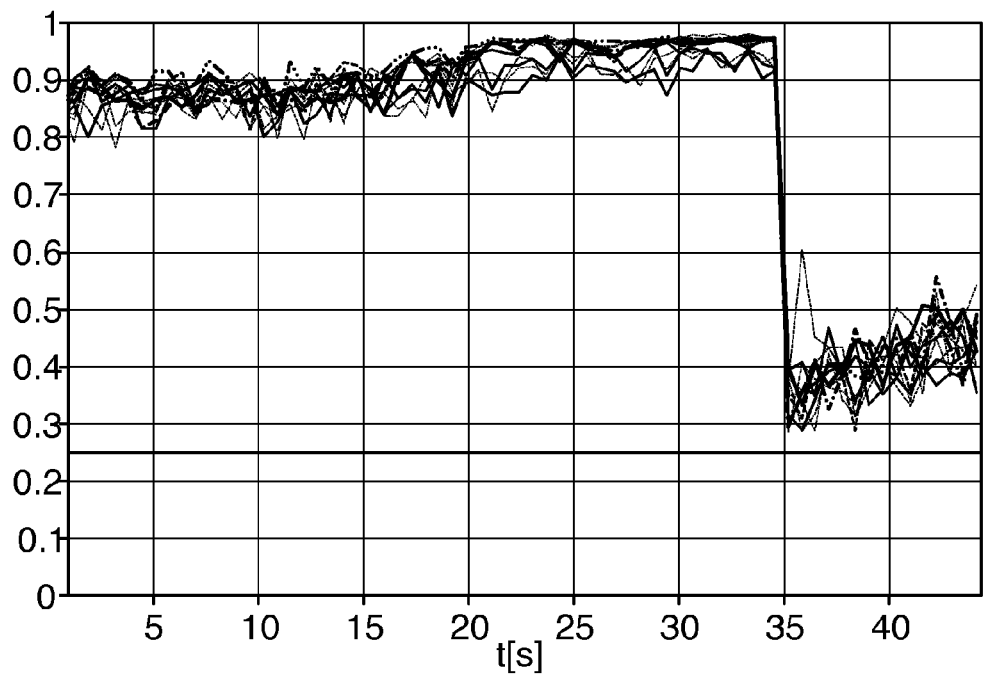
FIG. 9 shows the evolution in time of the autocorrelation coefficient of the time signals of the pressure sensors in the case of a load throw-off.
Figure 10:
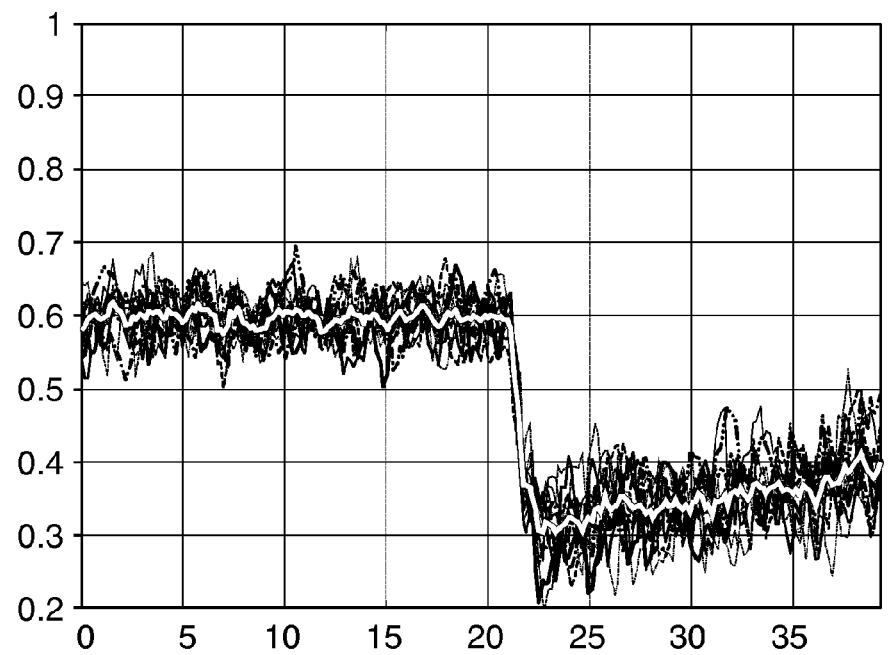
FIG. 10 shows the evolution in time of the autocorrelation coefficient of the time signals of the pressure sensors in the case of a controlled gas turbine shutdown.

FIGS. 9 and 10 show the expected variation with time of the autocorrelation coefficients for a total of twelve different combustors, based on measured cross-correlation values. The autocorrelation coefficient is in this case the expected correlation coefficient of the signals of two time segments of the same combustor that are offset with respect to one another. The autocorrelation coefficient is in each case plotted against the time in seconds.

FIG. 9 shows, analogously to FIG. 3, the variation with time for a trip. A fast shutdown of the gas turbine with interruption of the fuel supply to the combustors takes place at approx. 34 seconds. The graph shows an increase in the coherence up to almost the value 1 from second 25, which signifies a high flame intensity. This corresponds to the expected highly dynamic state during a trip. However, the increase is not quite so clear as in FIG. 3, i.e. in the case of the cross-correlation of two sensors. From the moment of the fast shutdown in which the flames are extinguished, the coherence decreases to a value around approx. 0.35. Deflections of individual signals above 0.5 also occur, however. Here too, therefore, higher coherence values with extinguished flames are produced compared to FIG. 3.

A similar picture with even clearer differences results in FIG. 10. FIG. 10 shows, analogously to FIG. 4, the variation with time of the correlation coefficients of the combustors for a routine controlled shutdown of the gas turbine. During routine operation the correlation coefficients vary between 0.5 and 0.7, i.e. approx. 0.1 lower than in the case of the cross-correlation between two sensors. In the event of a shutdown of the gas turbine with stopping of the fuel supply to the combustors at second 22, the correlation coefficient falls rapidly to values around approx. 0.35, likewise again with deflections above 0.5.

Overall, therefore, the autocorrelation of one sensor still allows a stable inference to be made with regard to the current flame state. However, the resulting values are not as clear as in the correlation of two independent sensors and the threshold values must be adjusted accordingly. Thus, if two sensors are provided per combustor, the autocorrelation should be used only if one sensor fails. On the other hand, the use of the autocorrelation makes it possible for existing gas turbines having only one pressure sensor per combustor to undergo a software-side retrofit.

Single Sensor Methods

The use of autocorrelation and other single-sensor methods makes possible the detection and monitoring of combustor flames using only one sensor per combustor, reducing the costs of sensors and associated wiring and interfacing. Furthermore, gas turbine control has been trending toward the use of only one sensor per combustor. Single sensor flame monitoring makes possible the implementation of flame monitoring in such new turbines without installing additional sensors.

Figure 11:
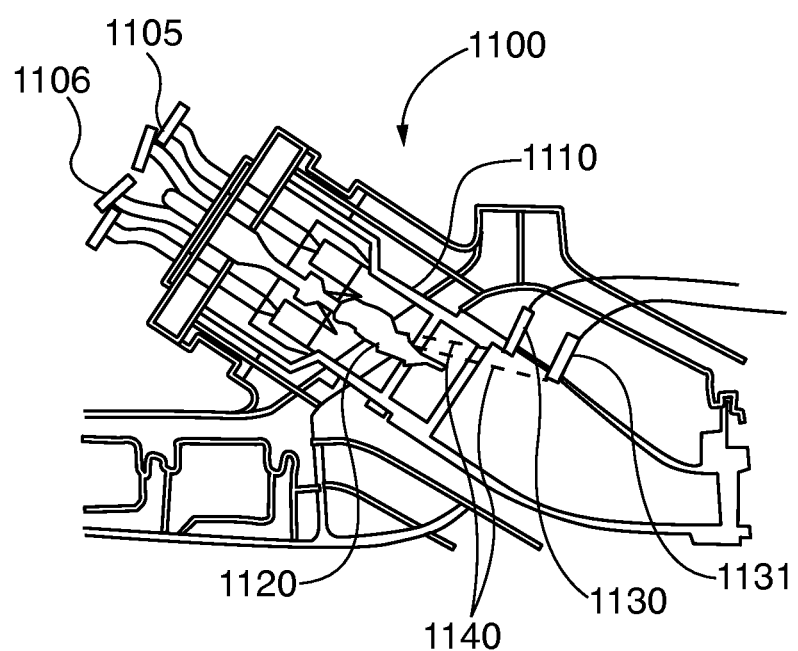
FIG. 11 shows a cross section of a gas turbine engine combustor according to one embodiment of the invention.

The above-described flame detection technique using dynamic pressure sensors utilizes data from two sensors per combustor to detect a flame-off condition in all combustors simultaneously. A summary of that concept is reviewed here with reference to a sectional view of the combustor 1100 of FIG. 11. Fuel introduced through the ports 1105, 1106 is mixed with compressed air in the combustor 1110 and ignited, creating a flame 1120. Two dynamic pressure sensors 1130, 1131 receive acoustic oscillations 1140 generated by the flame 1120 and convert those oscillations into signals that can be analyzed by a processor. As described above, the status of the flame 1120 can be reliably detected and monitored by combining information about the locations of the sensors 1130, 1131 and the flame 1120 with the spectral content contained in the sensor signals. The assumption is made that without the flame 1120 there exists no acoustic source at the flame location that emits spectral content similar to the flame. That concept has been validated on sensor data from a real gas turbine installation.

Figure 12:
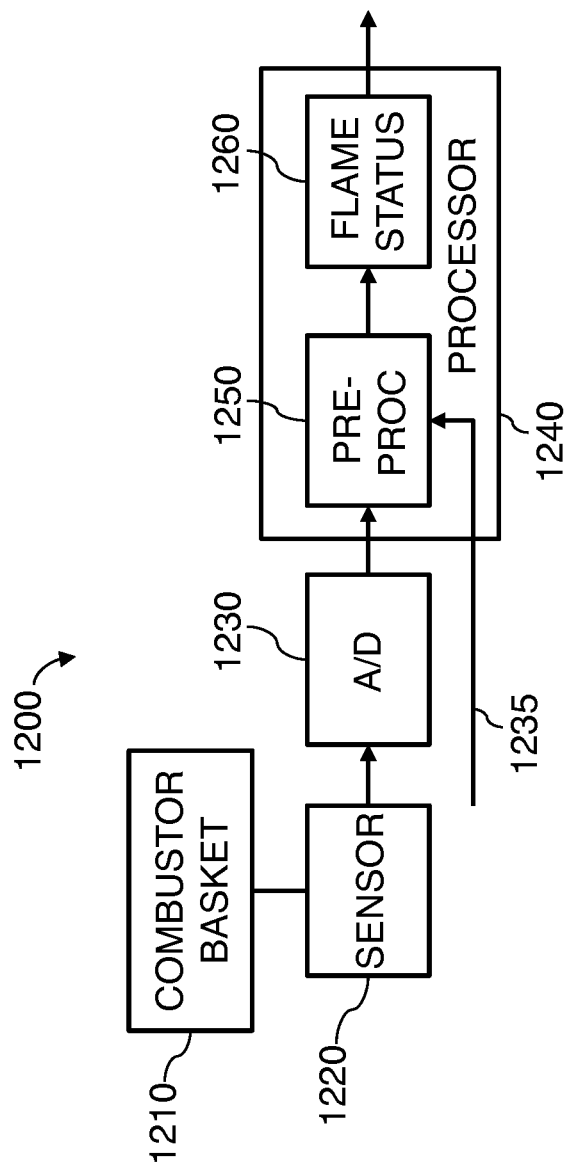
FIG. 12 is a block diagram of a method for monitoring a flame state in a gas turbine according to one embodiment of the invention.

A block diagram 1200, shown in FIG. 12, summarizes the disclosed methods for determining flame status using a single sensor 1220 per combustor 1210. An analog signal received from the sensor is converted to a digital signal by an analog-to-digital (A/D) converter 1230. The converter may, for example, be contained within an industrial programmable logic controller (PLC) used to control the gas turbine. The digital signal is then transmitted to a processor 1240, which may also be a processor within a PLC. Additional signals 1235 from other single sensors in other combustors (not shown) may also be transmitted to the processor 1240. The digital signal may be prepared by a preprocessor 1250 such as by filtering, scaling, or smoothing. The preprocessed digital signal is then received by a flame status determination algorithm 1260 in the processor 1240 for making a determination of flame status. The determination is generally an "on" or "off" determination. The determination may be used by the industrial PLC to generate alarms or take other action.

Single Sensor Autocorrelation

Figure 13A:
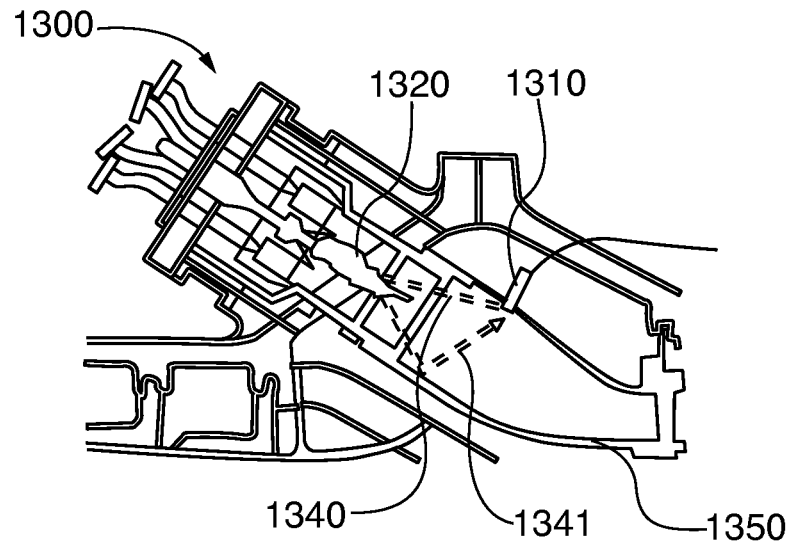
FIG. 13A shows a cross section of a gas turbine engine combustor according to one embodiment of the invention.

In cases where only one dynamic pressure sensor per combustor is available, one solution for monitoring flame status is to utilize reflections from the walls of the combustor that act as virtual microphones. A sectional view of a turbine combustor 1300, shown in FIG. 13A, is used to visualize that concept. A dynamic pressure sensor 1310 receives acoustic oscillations from the flame 1320 through the direct path 1340 as well as through an indirect path 1341 including reflections from the combustor wall 1350. The signal contribution from the reflections is delayed compared to the direct path as the reflected sound travels longer distances.

A graph 1360 (FIG. 13B) of a time response to an impulse signal, measured by a sensor in a basket of a micro turbine, illustrates this flame monitoring principle. The graph shows the signal that would be observed by a dynamic pressure sensor if one would emit a short signal pulse. The graph 1360 demonstrates that the impulse is not only observed once as a direct signal 1370 but also through multiple reflections as indirect signals 1380. The delays of the reflections are dependent on the physical dimensions of the combustor as well as the source (flame) and receiver (sensor) locations, which are fixed, and also on the gas properties such as temperature, gas composition and flow. That is, the impulse response from the flame location to the dynamic pressure sensor is varying due to changing gas properties during operation.

Note that an equal change of the gas properties over all locations inside the burner results in an equal change of the speed of sound and thus a uniform stretching or compression of the impulse response. In real turbine operation, however, the temperature and flow are distributions rather than constant values. Some signal paths are therefore affected more strongly than others by changes in gas properties, resulting in a warping of the impulse response. Inasmuch as the true flame signal is not known, it can be difficult to accurately predict the impulse response using a single sensor. It is known, however, that the gas parameters are limited to a physically feasible range. Furthermore, the geometry of the turbine combustor and, if present, the basket, is fixed. That allows the prediction of a time delay range in which it is physically possible for the main reflections to be observed. In the following representation of the recorded signal x(t) it is assumed that the recorded signal is a linear combination of the source signal s(t) and its time delayed reflections $[s_1(t-t_1), s_2(t-t_2), \ldots, s_N(t-t_N)]$:

$$x(t) = s(t) + \sum_{n=1}^{N} s_n(t - t_n).$$

That expression may be simplified by separating the amplitude a from the reflections: $s_1(t-t_1) \rightarrow a_1 * s(t-t_1)$. Then $$x(t) = s(t) + \sum_{n=1}^{N} (a_n * s(t - t_n))$$

Figure 13B:
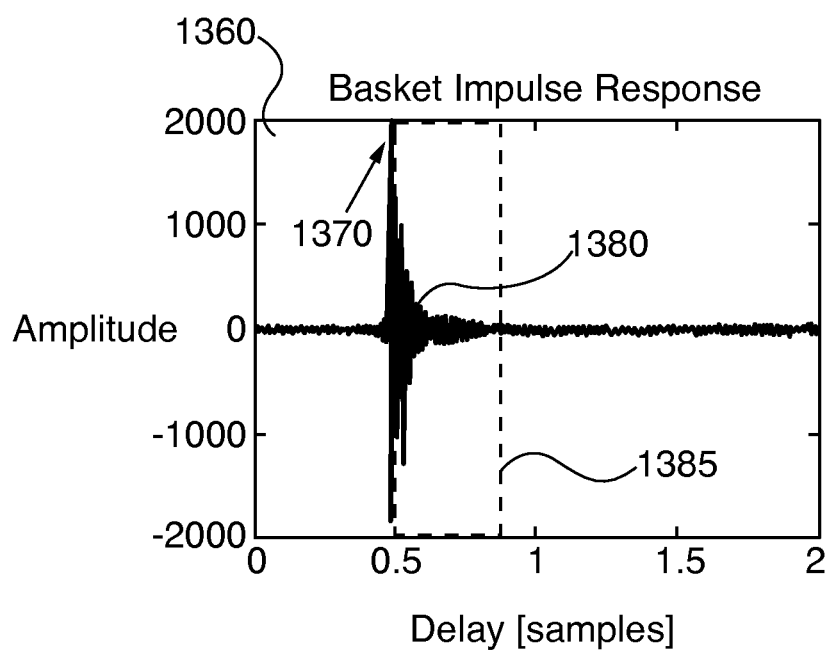
FIG. 13B shows the evolution in time of a combustor acoustic impulse response.

In the presently disclosed autocorrelation method, the reflections $s(t-t_n)$ that maximally correlate with the direct path signal s(t) are extracted. Specifically, the time delays of the reflection paths are limited to the physically possible range, represented by line 1385 of FIG. 13B, given the minimum and maximum gas parameters and the physical dimensions of the burner and combustor. Signals indicating reflection paths falling outside that range are ignored. Thereafter, the flame status can be monitored by correlating the spectral content of the flame from the reflected to the direct path signal.

Figure 14A:
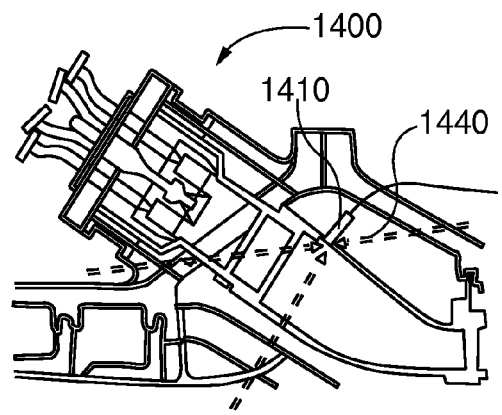
FIG. 14A shows a cross section of a gas turbine engine combustor according to one embodiment of the invention.

A cross-sectional view of a combustor 1400, shown in FIG. 14A, illustrates a scenario wherein no flame is present but there exists acoustic noise from outside the combustor 1400. The presently described technique assumes that the external acoustic noise 1440 received by the sensor 1410 is not coming from the same combination of locations where the flame signal is reflected from the inner burner walls. Furthermore, the technique assumes that different acoustic noise sources are uncorrelated and do not emit in the frequency range of the flame signal. Therefore, the single-sensor flame detection method can distinguish external and internal noise from a flame signal and thus detect flameout.

Figure 14B:
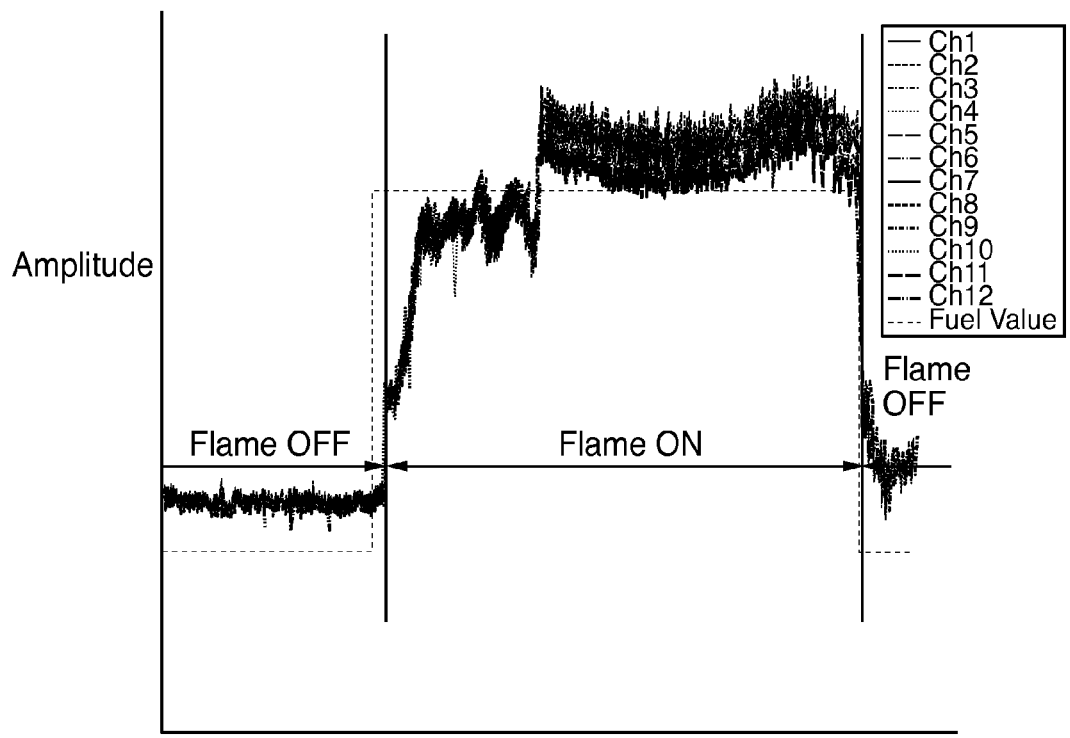
FIG. 14B is a diagram showing acoustic sensor autocorrelation over time during a fast shutdown of a gas turbine.

A graph 1460, shown in FIG. 14B, shows autocorrelation values on a time axis for a trip, or fast shutdown, of a gas turbine. After autocorrelation stabilizes in all combustors, the fuel supply is interrupted to all combustors. From the time of the trip, autocorrelation decreases rapidly to a measurably lower value.

Figure 15:
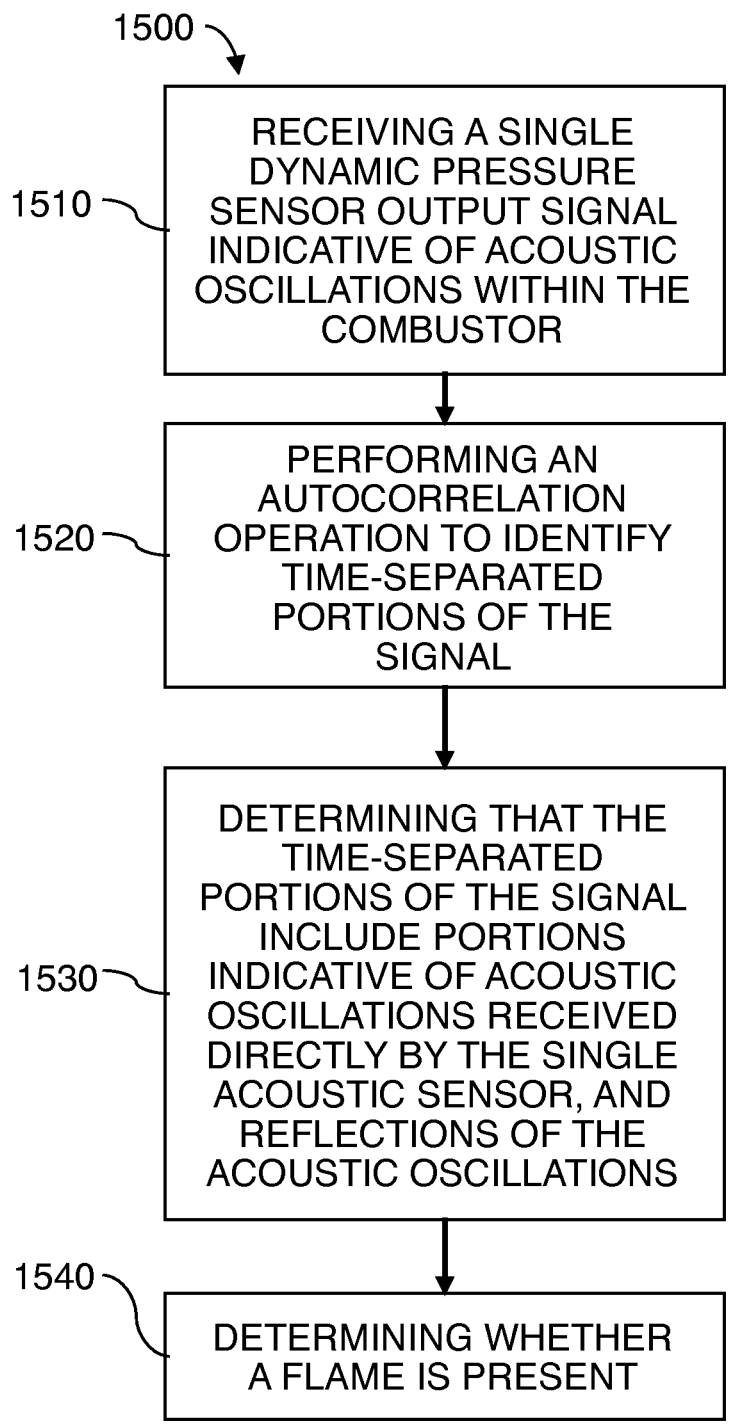
FIG. 15 is a flow chart showing a method according to one embodiment of the invention.

A flow chart 1500, shown in FIG. 15, illustrates one method in accordance with the autocorrelation technique described herein. A dynamic pressure sensor output signal is received at block 1510 from a single acoustic sensor positioned in the gas turbine engine combustor. The output signal is indicative of acoustic oscillations within the gas turbine engine combustor. As discussed above, that output signal may be filtered to exclude frequencies outside an expected frequency range emitted by the flame in the gas turbine engine combustor. The dynamic pressure sensor output signal may be received in time-based data blocks, such as blocks having a time period of 1 second or less.

An autocorrelation operation is performed at block 1520 on the dynamic pressure sensor output signal to identify time-separated portions of the signal. Each time-separated portion of the signal is assigned an autocorrelation value. In one embodiment, useful for monitoring during an ignition sequence, the autocorrelation operation comprises computing representations of oscillations in the output signal and weighting the representations with the autocorrelation values. The representations may comprise root mean squares, logarithms or sinusoidal weighted representations.

In order to limit the analysis of acoustic reflections to reflections that are physically possible within the combustor, the time-separated portions of the signal may be filtered to exclude portions having a delay range longer than a maximum threshold delay range. The maximum threshold delay range is based on physical dimensions of the gas turbine engine combustor and a maximum expected speed of sound in the gas turbine engine combustor.

Based on the autocorrelation values, a determination is made at block 1530 that the time-separated portions of the signal include portions indicative of acoustic oscillations emitted by the flame in the gas turbine engine combustor and received directly by the single acoustic sensor, and portions indicative of reflections of the acoustic oscillations emitted by the flame. The determination may be made by determining that the autocorrelation values of the time-separated portions of the signal fall above an autocorrelation value threshold. The autocorrelation value threshold may, for example, be a value greater than 0.5.

Based on the determination that the time-separated portions of the signal include portions indicative of acoustic oscillations emitted by the flame in the gas turbine engine combustor and received directly by the single acoustic sensor, and portions indicative of reflections of the acoustic oscillations emitted by the flame, the technique determines at block 1540 whether a flame is present in the gas turbine engine combustor.

Dual Combustor Cross-Correlation

Figure 16:
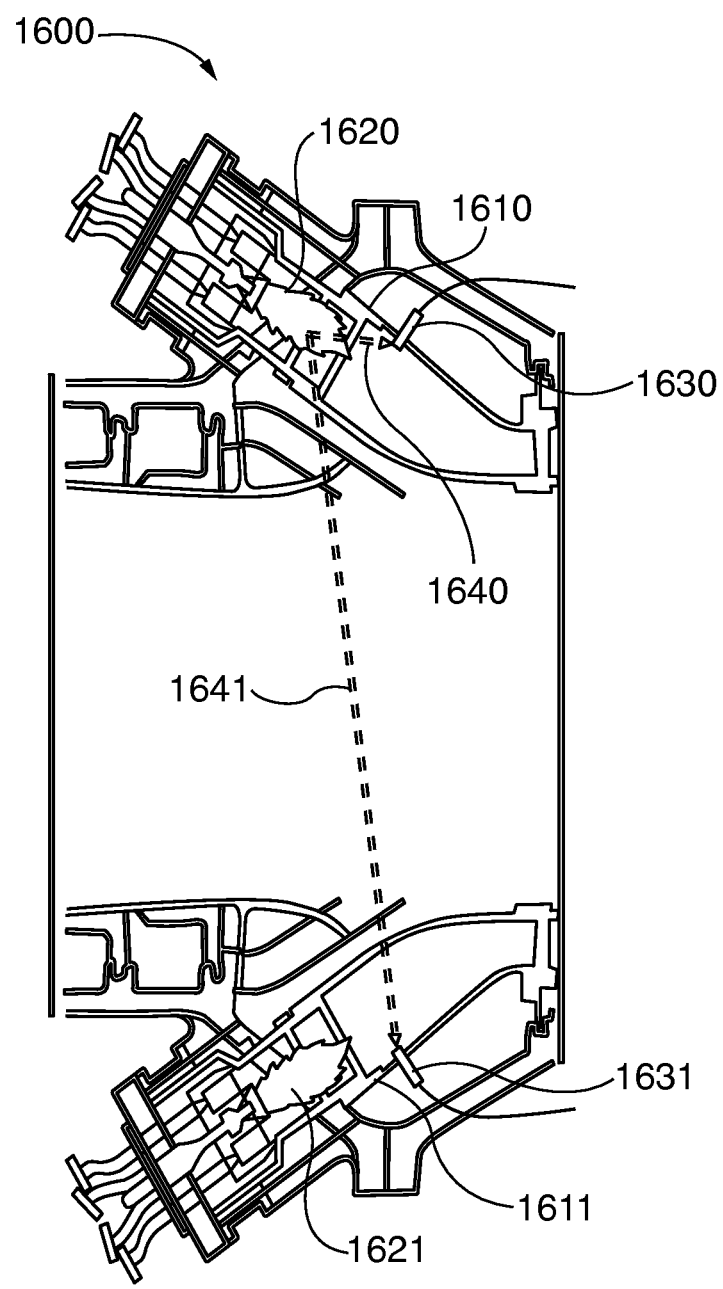
FIG. 16 shows a cross section of a gas turbine engine combustor according to one embodiment of the invention.

In an alternative signal processing technique for flame monitoring using a single dynamic pressure sensor per combustor, the signal coherence between combustors is utilized. In the combustion chamber 1600 shown in FIG. 16, a flame 1620 is burning in combustor 1610 and a flame 1621 is burning in combustor 1611. A dynamic pressure sensor 1630 records acoustic emissions present in combustor 1610 and a dynamic pressure sensor 1631 records acoustic emissions present in combustor 1611. In addition to receiving direct and reflected acoustic oscillations such as oscillations 1640, the sensor 1630 also receives oscillations 1641 created by the flame 1621 in combustor 1611 and propagated to the combustor 1610 containing the receiving sensor. Similar cross-propagated oscillations are received by the other sensors. The cross-correlation between the dynamic pressure signal 1640 received by the sensor in the combustor 1610 of the monitored flame 1620 and a time delayed dynamic pressure signal 1641 of the monitored flame received by a sensor 1631 in another combustor 1611 is evaluated to determine flame status. The flame 1620 is considered online if the cross-correlation of the two signals is above a threshold. The physically possible time delay for the acoustic signal 1641 to arrive at the dynamic pressure sensor 1631 of the other combustor 1611 is calculated and used to constrain the problem by filtering irrelevant signals.

Figure 17:
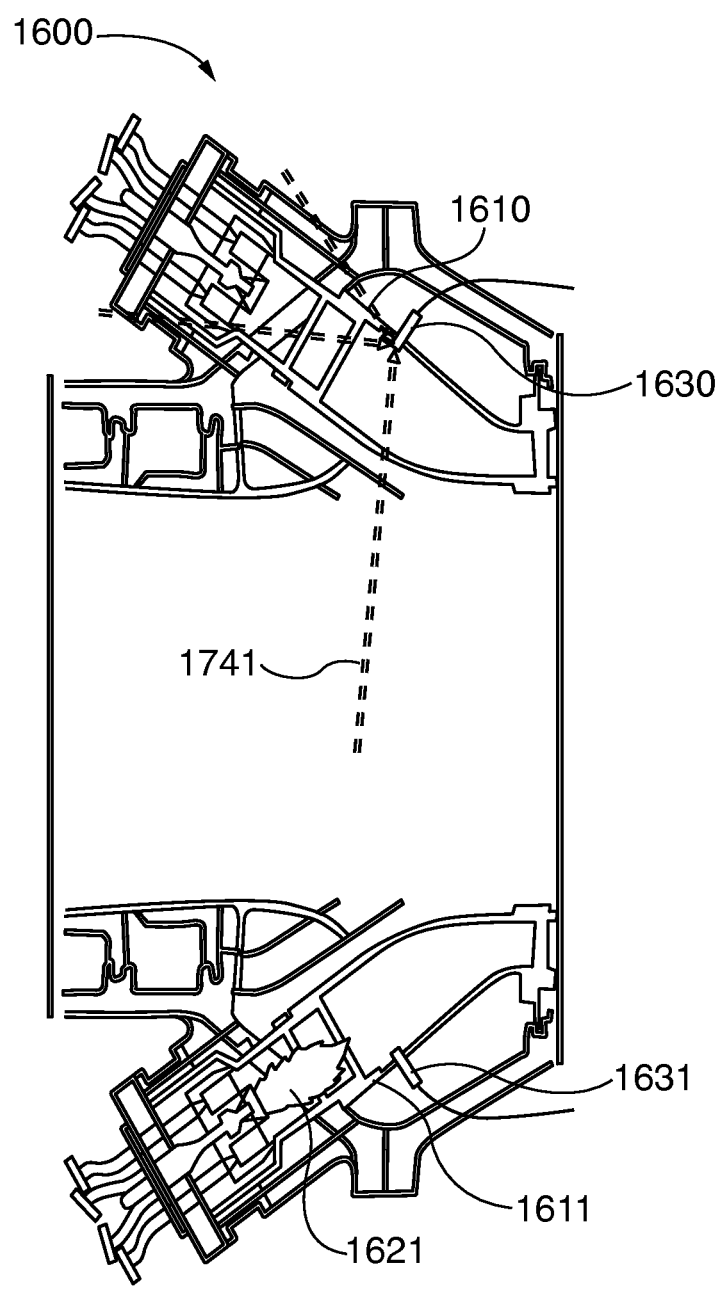
FIG. 17 shows a cross section of a gas turbine engine combustor according to one embodiment of the invention.

The same flame monitoring arrangement for the combustion chamber 1600 may be used to detect a condition in which only one of the two illustrated combustors contains a flame, as shown in FIG. 17. Note that while the lower combustor 1611 contains a flame 1621, there is no flame in the upper combustor 1610, and therefore no dynamic pressure signal from the combustor 1610 that is received in either of the dynamic pressure sensors 1630, 1631.

The time delay constraint ensures that the correlation of the dynamic pressure signal 1741 from the flame 1621 in the lower combustor 1611 does not result in a falsely detected flame signal in upper combustor 1610. That is, the time delay of a dynamic pressure signal from a flame in the upper combustor 1610 to its nearest dynamic pressure sensor 1630 is assumed to be shorter than the delay from that flame location to the dynamic pressure sensor 1631 in the lower combustor 1611. On the other hand, the acoustic waves from the flame 1621 in the lower combustor 1611 would first arrive at the dynamic pressure sensor 1631 in the lower combustor 1611. Thus the two scenarios can be distinguished and the combustor without flame can be detected. This technique assumes that the autocorrelation of the monitored flame signal components is narrow enough to distinguish between signals from different combustors.

Figure 18:
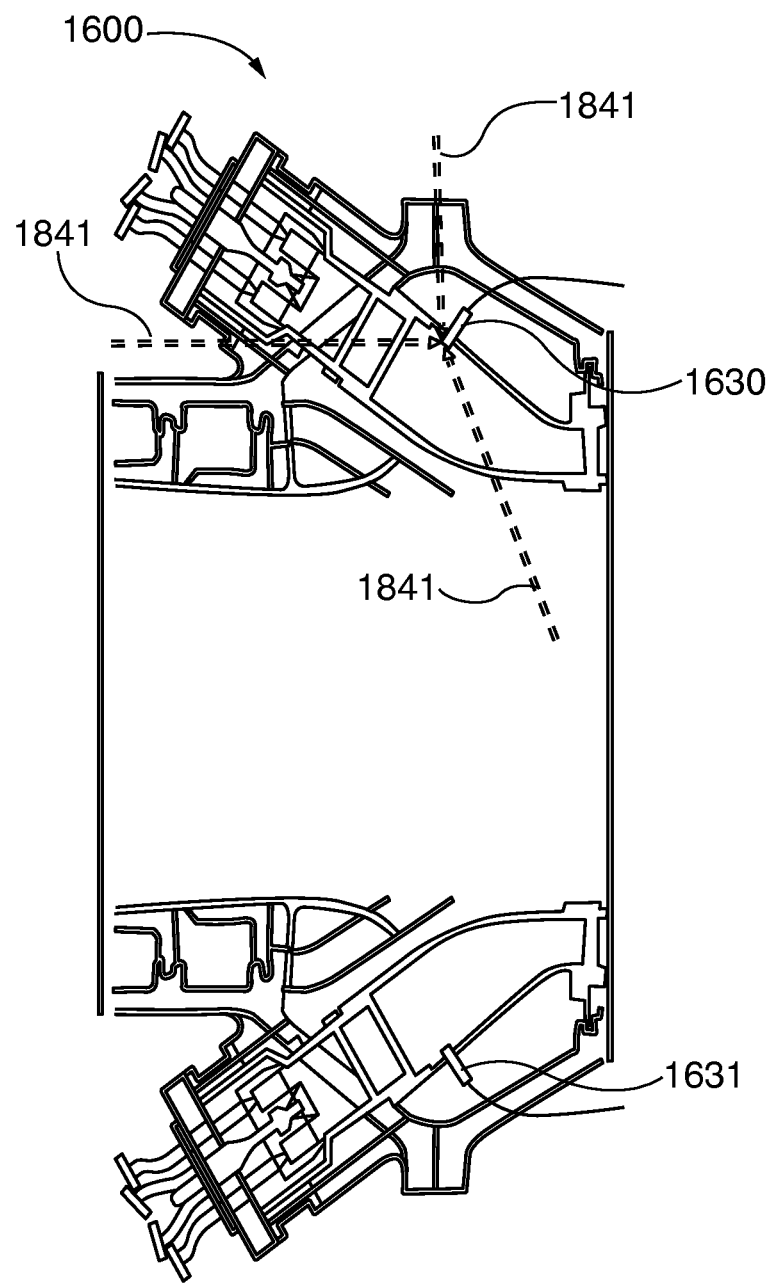
FIG. 18 shows a cross section of a gas turbine engine combustor according to one embodiment of the invention.

The presently described arrangement is also effective in determining flame status in the scenario where all flames in all combustors are off, as illustrated in FIG. 18. In that case, there exists only uncorrelated acoustic noise 1841 that does not match the physically motivated time delay range for acoustic waves to travel from a flame to the respective dynamic pressure sensors 1630, 1631. It is further assumed that the spectral content of the acoustic noise 1841 is distinguishable from a flame signal, providing an additional criterion for identifying the acoustic noise.

Figure 19:
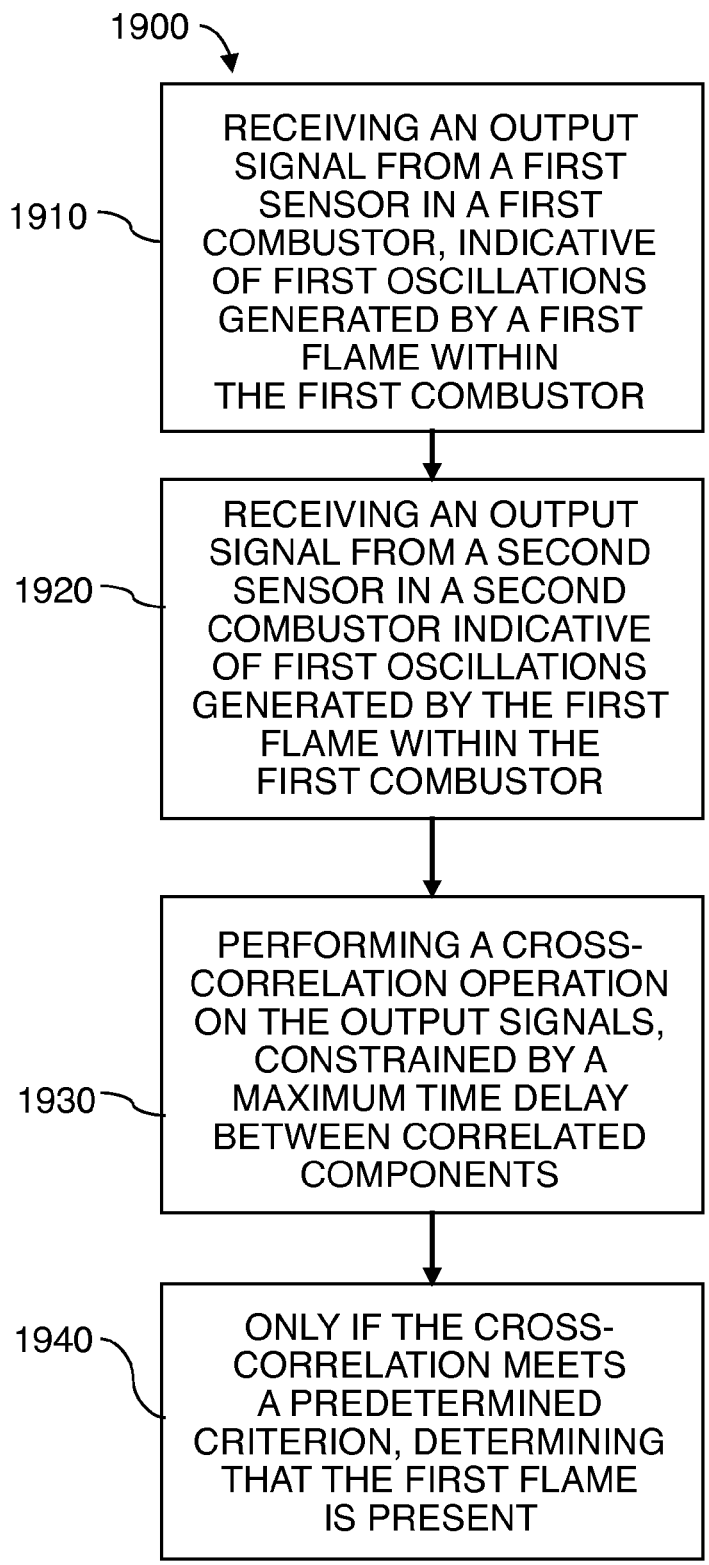
FIG. 19 is a flow chart showing a method according to one embodiment of the invention.

The flow chart 1900, shown in FIG. 19, illustrates one method in accordance with the above-described dual combustor cross-correlation technique. The method monitors flames in a plurality of gas turbine engine combustors arranged for combusting fuel in a gas turbine engine. At blocks 1910 and 1920, a processor receives dynamic sensor output signals from first and second acoustic sensors positioned in a first and second gas turbine engine combustors, respectively. The sensor outputs both contain information indicative of acoustic oscillations generated by a first flame within the first gas turbine engine combustor. In the case of the first sensor, the acoustic oscillations propagate within the combustor from the flame to the sensor. In the case of the second sensor, the acoustic oscillations propagate from the flame in the first combustor, across space between the first and second combustors, to the second sensor in the second combustor.

The dynamic sensor output signals may be received in data blocks of 1 second or less in length. To increase efficiency and speed, the first and second dynamic sensor output signals may be filtered to exclude frequencies outside an expected frequency range emitted by the first flame within the first gas turbine engine combustor.

The processor then performs a cross-correlation operation on the first and second dynamic sensor output signals at block 1930, to determine a cross-correlation value between the first and second acoustic oscillations. The cross-correlation operation is constrained by a maximum time delay between correlated components of the first and second acoustic oscillations. The maximum time delay is based on the physical parameters of the system. For example, it may be based on the physical geometry of the gas turbine engine combustors and the maximum expected speed of sound in the gas turbine engine combustors.

The cross-correlation operation on the dynamic pressure sensor output signals may further include computing representations of oscillations in the output signals, and weighting the representations with the cross-correlation values. The representations may comprise root mean squares, logarithms or sinusoidal weighted representations.

A determination is then made at block 1940 whether a flame is present in the first combustor. Only if the cross-correlation value meets a predetermined criterion, a determination is made that the flame is present. Otherwise, the processor determines that a flame-out condition exists. For example, the criterion may be a threshold cross-correlation value such as 0.2. In that case, if the cross-correlation value is below 0.2, it is determined that there is no flame in the combustor. Other criteria may be used to determine flame-out, such as a steepness of a drop in cross correlation value over time, or a difference between two combustors.

As noted, at a given sensor, oscillations from the flame in the same combustor can be distinguished from oscillations from flames in other combustors by the order the oscillations are received between two sensors. For example, if first acoustic oscillations generated by a first flame reach a first acoustic sensor before second acoustic oscillations generated by the first flame reach a second acoustic sensor, then it can be concluded that the second acoustic oscillations are generated by the first flame.

The two sensors may be used to monitor flames in both combustors by detecting oscillations from both flames. Specifically, in addition to the above, a third dynamic sensor output signal is received from the first acoustic sensor positioned in the first gas turbine engine combustor. The third dynamic sensor output signal contains components indicative of third acoustic oscillations generated by a second flame within the second gas turbine engine combustor and propagated to the first acoustic sensor positioned in the first gas turbine engine combustor. Further, a fourth dynamic sensor output signal is received from the second acoustic sensor positioned in the second gas turbine engine combustor. The fourth dynamic sensor output signal contains components indicative of fourth acoustic oscillations generated by the second flame within the second gas turbine engine combustor. A cross-correlation operation is performed on the third and fourth dynamic sensor output signals to determine a cross-correlation value between the third and fourth acoustic oscillations. The cross-correlation operation is constrained by a maximum time delay between correlated components of the third and fourth acoustic oscillations. A determination is made that the second flame is present within the second gas turbine engine combustor only if the cross-correlation value meets a predetermined criterion.

The duration of an autocorrelation of the first dynamic sensor output signal is preferably sufficiently narrow to permit distinguishing the signal components indicative of the first acoustic oscillations from the signal components indicative of the third acoustic oscillations.

Characteristic Spectral Pattern

Another technique for processing the dynamic pressure sensor output signals for flame detection does not rely on the time delay of the various signal paths from the flame to the dynamic pressure sensor, Instead, it is possible to monitor the spectral characteristics of the flame at the dynamic pressure sensor location. There are two phenomena that make that possible. First, each flame emits energy with a unique and characteristic spectral pattern. Second, as noted above, the acoustic oscillations received by the sensors include both direct and reflected signals. For the different frequencies contained in a signal, the different path lengths of the reflections result in constructive or destructive signal contributions at the sensor location. For example, if a signal of frequency $F_1$ arrives at the sensor through the direct path with the same amplitude as a reflected signal in which the reflected path introduces a delay of $2/F_1$ (i.e., a 180 degree phase shift), the direct path signal is canceled by the contribution of the reflected signal and the sensor cannot see a signal at the frequency $F_1$.

Figure 20:
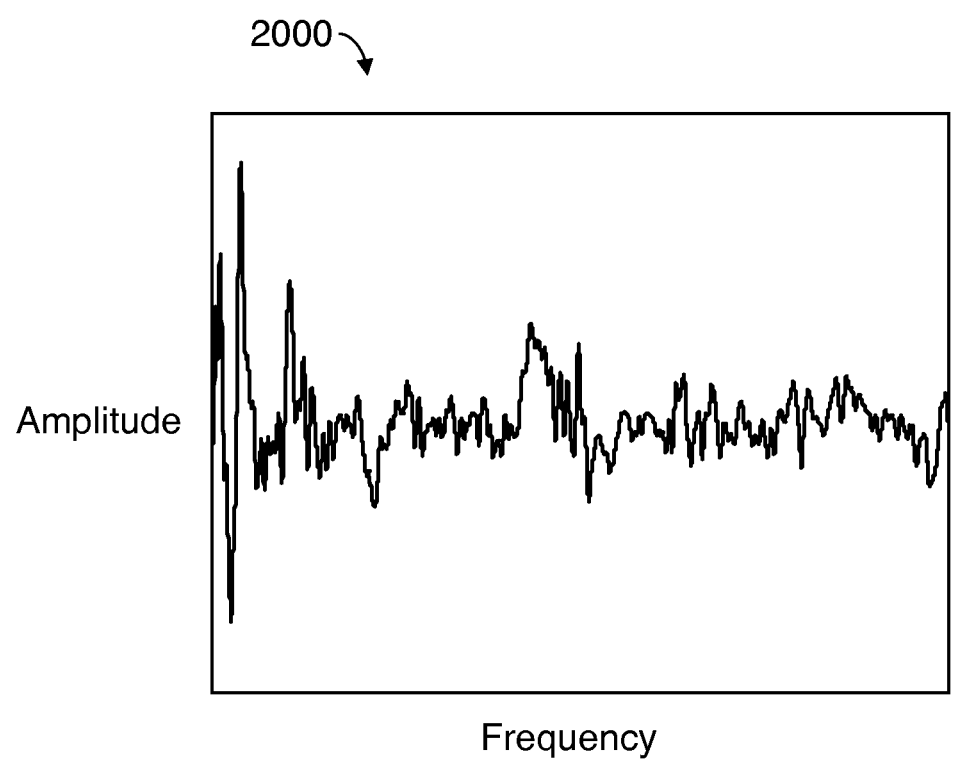
FIG. 20 is a chart showing an extracted frequency pattern representing a flame according to one embodiment of the invention.

The acoustic oscillations received at a sensor are therefore a function of the individual acoustic properties of the flame and also of the basket or combustor geometry. A "frequency key" or characteristic pattern that includes both the spectral pattern of the flame and information on the cancellation may be used to identify and detect the flame in the combustor. An example spectral characteristic pattern 2000, illustrated in FIG. 20, was extracted to represent the flame in a burner. By multiplying that pattern with new data one can determine the current flame status.

One possibility for extracting such a characteristic pattern is to apply feature extraction techniques to known ground-truth training data. In one technique, spectral patterns are recorded at the sensor location when the corresponding flame is burning and when the flame is off line. Those samples are processed using a feature extraction algorithm. One can also provide training data for difficult-to-detect operational states such as for an all-combustor-shutdown where the engine remains very noisy but all flames are off line. Additionally, the feature extraction algorithm is provided with information on the flame state (1=On, 0=Off) for each ground-truth spectral pattern. The feature extraction algorithm is then used to find a reduced representation set of spectral features that links the input spectral pattern to the flame state.

To analyze a live sensor feed, distances are calculated from a spectral representation of the sensor signal to the patterns linked to each flame state. The closest match is then selected. In one example, a projection technique is used. That is, if one multiplies the extracted spectral characteristic with the input spectral pattern from a sensor feed, one receives the flame state within some small error. Characteristics associated with a flame-on condition, when multiplied by the extracted spectral characteristic, yield a value close to 1. Characteristics associated with an off-line flame condition, and characteristics associated with noise, when multiplied by the extracted spectral characteristic, yield a value close to 0. Note that one could use distance measures other than a projection to evaluate the similarity of the extracted spectral characteristics and the currently monitored frequency pattern. Examples include a sum of the squared distances, an L1 distance, etc.

Methods for extracting a characteristic function include, for example, Linear Discriminant Analysis (LDA), Canonical Correlation Analysis (CCA) and Generalized Mutual Interdependence Analysis (GMIA), described in H. Claussen, J. Rosca & R. Damper, Signature extraction using mutual interdependencies, 44 Pattern Recognition 650 (2011), which is incorporated by reference herein. Note that these methods are applied on high dimensional data vectors with each frequency component representing one component of the vector.

Figure 21:
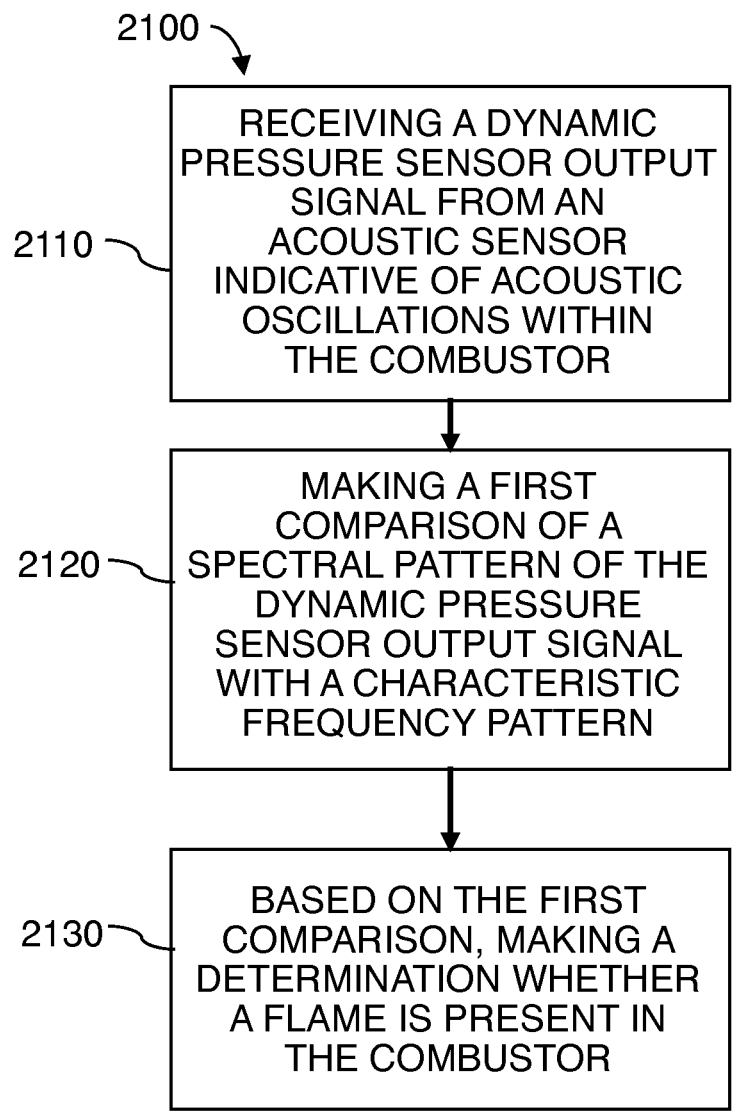
FIG. 21 is a flow chart showing a method according to one embodiment of the invention.

A flow chart 2100, shown in FIG. 21, shows an example method for monitoring a flame in accordance with the above-described characteristic spectral pattern technique. A dynamic pressure sensor output signal is received at block 2010 from an acoustic sensor positioned in the combustor. The output signal contains components that are indicative of acoustic oscillations within the combustor. The dynamic pressure sensor output signal may be filtered to exclude frequencies outside an expected frequency range emitted by the flame in the combustor.

A spectral pattern of the dynamic pressure sensor output signal is compared, at block 2120, with a characteristic frequency pattern that includes information about an acoustic spectral pattern of the flame and information about acoustic signal canceling due to reflections of the dynamic pressure sensor output signal within the combustor. The spectral pattern of the dynamic pressure sensor output signal may also be compared with a characteristic frequency pattern that includes information about an acoustic spectral pattern present in the combustor during a flame-out condition in the combustor. The characteristic frequency patterns may be based on training data with known ground truth regarding the flame conditions. Based on the comparison, a determination is made at block 2130 whether or not a flame is present in the combustor.

As discussed above, the characteristic frequency pattern may be determined using pattern recognition and feature extraction techniques. In one example, a first training spectral pattern of the dynamic pressure sensor output signal is recorded while the flame is burning, and a second pattern is recorded while the flame is not burning. The patterns may be recorded under a plurality of different regimes of combustor operation so that the determination whether a flame is present may be made under those respective regimes of operation.

A feature extraction analysis operation is performed on the two recorded training spectral patterns to identify a spectral characteristic that can be used to link a spectral pattern to a flame state. The determination is then made whether a flame is present in the combustor by evaluating a similarity of the spectral characteristic to the spectral pattern of the dynamic pressure sensor output signal. The similarity may be evaluated using a distance measure.

A third training spectral pattern may be recorded while no flame is burning in any combustor of the gas turbine engine combustion chamber. In that case, noise from other components, such as bearings, air turbulence and vibrations, is documented and differentiated from the acoustic characteristics of a flame in the combustor. The feature extraction analysis operation may, for example, be applied to a data vector wherein each component of the vector represents a frequency component of the spectral pattern of the dynamic pressure sensor output signal.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for monitoring a flame in a gas turbine engine combustor, comprising:
   receiving a dynamic pressure sensor output signal from an acoustic sensor positioned in the gas turbine engine combustor, the output signal being indicative of acoustic oscillations within the combustor;
   making a first comparison of a spectral pattern of the dynamic pressure sensor output signal with a characteristic frequency pattern that includes information about an acoustic spectral pattern of the flame and information about acoustic signal canceling due to reflections of the dynamic pressure sensor output signal within the combustor; and
   based on the first comparison, making a determination whether a flame is present in the combustor,
   wherein the first comparison is performed by multiplying the characteristic frequency pattern with the dynamic pressure sensor output signal.

2. The method of claim 1, further comprising:
   making a second comparison of the spectral pattern of the dynamic pressure sensor output signal with a characteristic frequency pattern that includes information about an acoustic spectral pattern present in the combustor during a flame-out condition in the combustor; and
   wherein making the determination is based on the first and second comparisons.

3. The method of claim 1, further comprising:
   filtering the dynamic pressure sensor output signal to exclude frequencies outside an expected frequency range emitted by the flame in the combustor.

4. The method of claim 1, wherein the characteristic frequency pattern is based on training data with known ground truth regarding flame condition.

5. The method of claim 1, further comprising constructing the characteristic frequency pattern by:
   recording a first training spectral pattern of the dynamic pressure sensor output signal while the flame is burning;
   recording a second training spectral pattern of the dynamic pressure sensor output signal while the flame is not burning; and
   performing a feature extraction analysis operation on the first and second training spectral patterns to identify a spectral characteristic that links a spectral pattern to a flame state; and
   wherein making the determination whether a flame is present in the combustor further comprises evaluating a similarity of the spectral characteristic to the spectral pattern of the dynamic pressure sensor output signal.

6. The method of claim 5, wherein evaluating a similarity comprises evaluating a distance measure.

7. The method of claim 5, wherein recording the first and second spectral training patterns comprises recording under a plurality of different regimes of combustor operation for use in determining whether a flame is present during operation of the combustor under the respective regimes of operation.

8. The method of claim 5, wherein:
   constructing the characteristic frequency pattern further comprises recording a third training spectral pattern of the dynamic pressure sensor output signal while no flame is burning in any combustor of a gas turbine engine combustion chamber; and
   performing a feature extraction operation on the first and second training spectral patterns further comprises performing a feature extraction operation on the third training spectral pattern.

9. The method of claim 5, wherein the feature extraction analysis operation is selected from a group consisting of linear discriminant analysis and generalized mutual interdependence analysis.

10. The method of claim 5, wherein the feature extraction analysis operation is applied to a data vector wherein each component of the vector represents a frequency component of the spectral pattern of the dynamic pressure sensor output signal.

11. A system for monitoring a flame in a gas turbine engine combustor, comprising:
    an acoustic sensor positioned for measuring acoustic oscillations within the gas turbine engine combustor;
    a processor connected for receiving a dynamic pressure sensor output signal from the acoustic sensor;
    computer readable media containing computer readable instructions that, when executed by the processor, cause the processor to perform the following operations:
        receiving a dynamic pressure sensor output signal from the acoustic sensor, the output signal being indicative of acoustic oscillations within the combustor;
        making a first comparison of a spectral pattern of the dynamic pressure sensor output signal with a characteristic frequency pattern that includes information about an acoustic spectral pattern of the flame and information about acoustic signal canceling due to reflections of the dynamic pressure sensor output signal within the combustor;
        based on the first comparison, making a determination whether a flame is present in the combustor,
        wherein the first comparison is performed by multiplying the characteristic frequency pattern with the dynamic pressure sensor output signal.

12. The system of claim 11, wherein the operations further comprise:
    making a second comparison of the spectral pattern of the dynamic pressure sensor output signal with a characteristic frequency pattern that includes information about an acoustic spectral pattern present in the gas turbine engine combustor during a flame-out condition in the combustor; and
    wherein making the determination is based on the first and second comparisons.

13. The system of claim 11, wherein the operations further comprise:
    filtering the dynamic pressure sensor output signal to exclude frequencies outside an expected frequency range emitted by the flame in the combustor.

14. The system of claim 11, wherein the characteristic frequency pattern is based on training data with known ground truth regarding flame condition.

15. The system of claim 11, wherein the operations further comprise constructing the characteristic frequency pattern by:
recording a first training spectral pattern of the dynamic pressure sensor output signal while the flame is burning;
recording a second training spectral pattern of the dynamic pressure sensor output signal while the flame is not burning; and
performing a feature extraction analysis operation on the first and second training spectral patterns to identify a spectral characteristic that links a spectral pattern to a flame state; and
wherein making the determination whether a flame is present in the combustor further comprises evaluating a similarity of the spectral characteristic to the spectral pattern of the dynamic pressure sensor output signal.

16. The system of claim 15, wherein evaluating a similarity comprises evaluating a distance measure.

17. The system of claim 15, wherein recording the first and second spectral training patterns comprises recording under a plurality of different regimes of combustor operation for use in determining whether a flame is present during operation of the combustor under the respective regimes of operation.

18. The system of claim 15, wherein:
constructing the characteristic frequency pattern further comprises recording a third training spectral pattern of the dynamic pressure sensor output signal while no flame is burning in any combustor of a gas turbine engine combustion chamber; and
performing a feature extraction operation on the first and second training spectral patterns further comprises performing a feature extraction operation on the third training spectral pattern.

19. The system of claim 15, wherein the feature extraction analysis operation is selected from a group consisting of linear discriminant analysis and generalized mutual interdependence analysis.

20. The system of claim 15, wherein the feature extraction analysis operation is applied to a data vector wherein each component of the vector represents a frequency component of the spectral pattern of the dynamic pressure sensor output signal.

\* \* \* \* \*